(12) United States Patent
Gangjee

(10) Patent No.: US 9,732,090 B2
(45) Date of Patent: Aug. 15, 2017

(54) BICYCLIC AND TRICYCLIC PYRIMIDINE TYROSINE KINASE INHIBITORS WITH ANTITUBULIN ACTIVITY AND METHODS OF TREATING A PATIENT

(71) Applicant: Duquesne University of the Holy Spirit, Pittsburgh, PA (US)

(72) Inventor: Aleem Gangjee, Allison Park, PA (US)

(73) Assignee: Duquesne University of the Holy Ghost, Pittsburgh, PA (US)

( * ) Notice: Subject to any disclaimer, the term of this patent is extended or adjusted under 35 U.S.C. 154(b) by 0 days.

(21) Appl. No.: 14/859,854

(22) Filed: Sep. 21, 2015

(65) Prior Publication Data

US 2016/0009731 A1    Jan. 14, 2016

Related U.S. Application Data

(62) Division of application No. 13/364,930, filed on Feb. 2, 2012, now Pat. No. 9,139,590.

(60) Provisional application No. 61/439,470, filed on Feb. 4, 2011.

(51) Int. Cl.
| | | |
|---|---|---|
| C07D 491/04 | (2006.01) |
| A61K 31/519 | (2006.01) |
| A61P 35/00 | (2006.01) |
| C07D 487/04 | (2006.01) |
| C07D 495/04 | (2006.01) |
| C07D 491/048 | (2006.01) |

(52) U.S. Cl.
CPC ......... *C07D 495/04* (2013.01); *C07D 487/04* (2013.01); *C07D 491/04* (2013.01); *C07D 491/048* (2013.01)

(58) Field of Classification Search
CPC ... C07D 487/04; C07D 491/04; A61K 31/519
USPC .................... 544/278, 280; 514/265.1, 260.1
See application file for complete search history.

(56) References Cited

U.S. PATENT DOCUMENTS

| 6,413,971 B1 | 7/2002 | Arnold et al. |
| 6,455,534 B2 | 9/2002 | Bridges et al. |
| 6,492,383 B1 | 12/2002 | Munchhof et al. |
| 2004/0058922 A1 | 3/2004 | Blumenkopf et al. |
| 2004/0063733 A1 | 4/2004 | Lambert et al. |
| 2005/0187389 A1 | 8/2005 | Milanov et al. |
| 2006/0276489 A1 | 12/2006 | Goff et al. |
| 2009/0082374 A1 | 3/2009 | Gangjee |

FOREIGN PATENT DOCUMENTS

| WO | 9727199 | 7/1997 |
| WO | 9823613 | 6/1998 |

OTHER PUBLICATIONS

Gangjee et al., Antiangiogenic and Antitumor Agents: Design, Synthesis, and Evaluation of Novel 2-Amino-4(3-bromoanilino)-6-benzylsubstituted Pyrrolo[2,3-dipryimidines as Inhibitors of Receptor Tyrosine Kinases; Bioorganic & Medicinal Chemistry, 2003, vol. 11, pp. 5155-5170.

Gangjee et al., Synthesis and Discovery of Water Soluble Microtubule Targeting Agents that Bind to the Colchicine Site on Tubulin and Circumvent Pgp Mediated Resistance; J.Med. Chem., 2010, vol. 53(22), pp. 8116-8128.

PCT International Search Report and Written Opinion of International Searching Authority for PCT/US12/23643, mailed Aug. 6, 2012.

Japanese Official Action dated Jan. 20, 2016 for JP 2015-100842.

*Primary Examiner* — Susanna Moore
(74) *Attorney, Agent, or Firm* — Eckert Seamans Cherin & Mellot, LLC; Carol A. Marmo

(57) ABSTRACT

Bicyclic and tricyclic pyrimidine tyrosine kinase inhibitors with antitubulin activity are provided in the present invention. The compositions of the present invention possess dual activity in a single agent of potent vascular endothelial growth factor receptor inhibitory activity as well as antitubulin activity. Water soluble salts of these compositions are also described. Methods of treating a patient having cancer, macular degeneration, and arthritis with the compositions and salts thereof of the present invention are disclosed.

7 Claims, 32 Drawing Sheets

Series I:
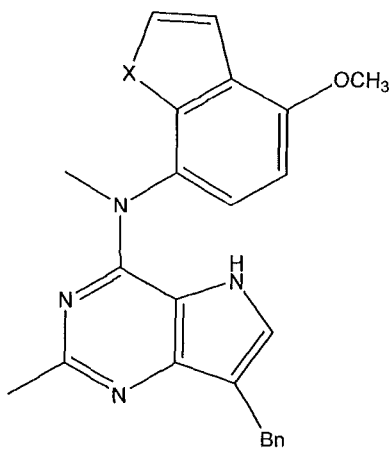
| COMPOSITION NUMBER | X | Bn |
|---|---|---|
| 4 | CH=CH | benzyl |
| 5 | NH | benzyl |
| 6 | NCH3 | benzyl |
| 7 | O | benzyl |
| 8 | S | benzyl |
Series IIa:
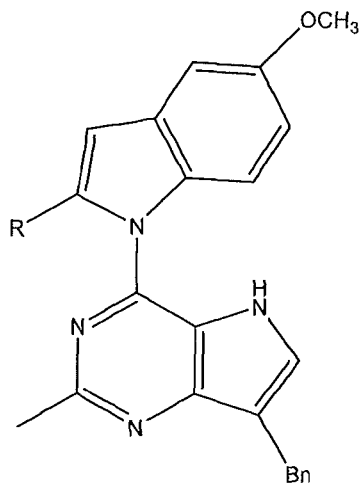
| COMPOSITION NUMBER | R | Bn |
|---|---|---|
| 15 | H | benzyl |
| 16 | CH3 | benzyl |
Figure 1

Series IIb:
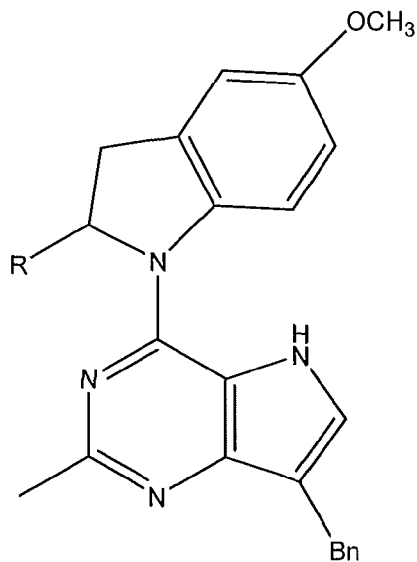
| COMPOSITION NUMBER | R | Bn |
|---|---|---|
| 17 | H | benzyl |
| 18 | $CH_3$ | benzyl |
Series III:
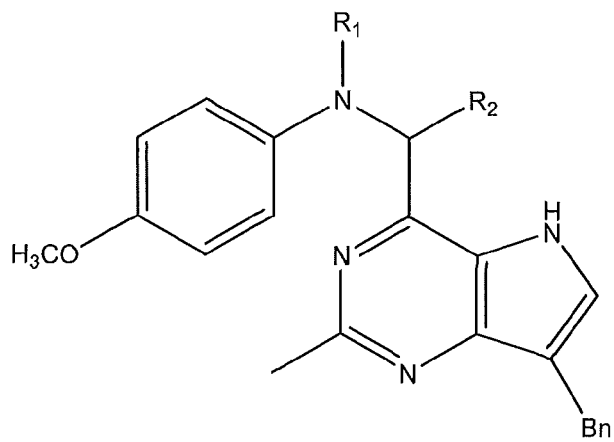
| COMPOSITION NUMBER | $R_1$ | $R_2$ | Bn |
|---|---|---|---|
| 22 | $CH_3$ | H | benzyl |
| 23 | $CH_3$ | $CH_3$ | benzyl |
| 24 | H | $CH_3$ | benzyl |
Figure 2

Series IV:
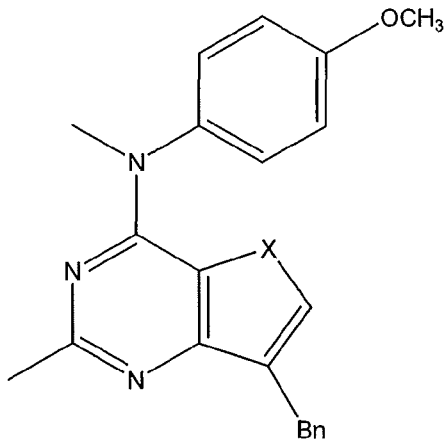
| COMPOSITION NUMBER | X | Bn |
|---|---|---|
| 27 | S | benzyl |
Series VIIIa:
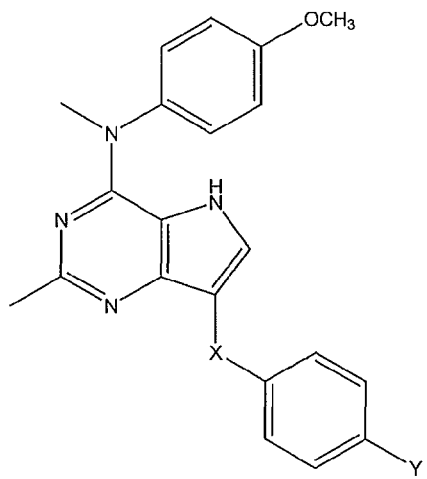
| COMPOUND NUMBER | X | Y |
|---|---|---|
| 50 | NH | H |
| 51 | NCH$_3$ | H |
| 52 | O | H |
| 53 | S | H |
| 54 | NH | OCH$_3$ |
| 55 | NCH$_3$ | OCH$_3$ |
| 56 | O | OCH$_3$ |
| 57 | S | OCH$_3$ |
Figure 3

Series VIIIb:
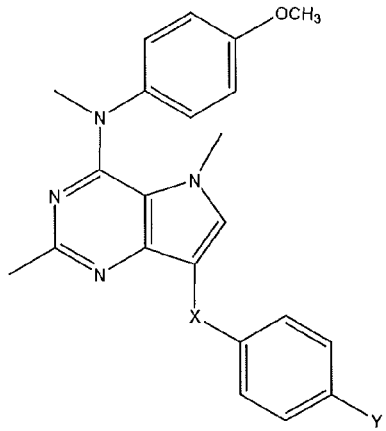
| COMPOSITION NUMBER | X | Y |
|---|---|---|
| 58 | NH | H |
| 59 | NCH$_3$ | H |
| 60 | O | H |
| 61 | S | H |
| 62 | NH | OCH$_3$ |
| 63 | NCH$_3$ | OCH$_3$ |
| 64 | O | OCH$_3$ |
| 65 | S | OCH$_3$ |
Series Xa:
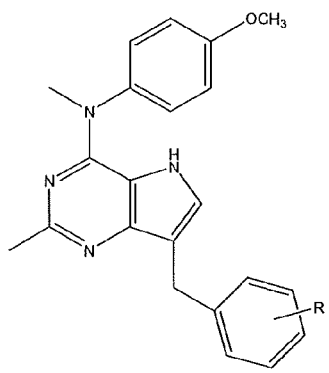
| COMPOSITION NUMBER | R |
|---|---|
| 74 | 2',6'-diCH$_3$ |
| 77 | 2',5'-diOCH$_3$ |
| 78 | 2',4'-diCl |
| 79 | 3',4'-diCl |
| 80 | 2',3'-(CH)$_4$ |
| 81 | 3',4'-(CH)$_4$ |
| 82 | 3',4',5'-triOCH$_3$ |
Figure 4

Series Xb:
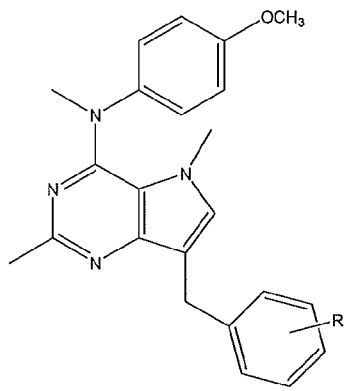
| COMPOSITION NUMBER | R |
|---|---|
| 83 | 2',6'-diCH$_3$ |
| 86 | 2',5'-diOCH$_3$ |
| 87 | 2',4'-diCl |
| 88 | 3',4'-diCl |
| 89 | 2',3'-(CH)$_4$ |
| 90 | 3',4'-(CH)$_4$ |
| 91 | 3',4',5'-triOCH$_3$ |
Series XI:
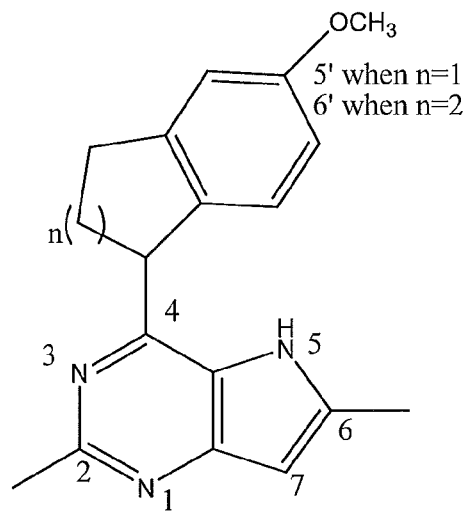
| COMPOSITION NUMBER | n |
|---|---|
| 92 | 1 |
| 93 | 2 |
Figure 5

Series XII:
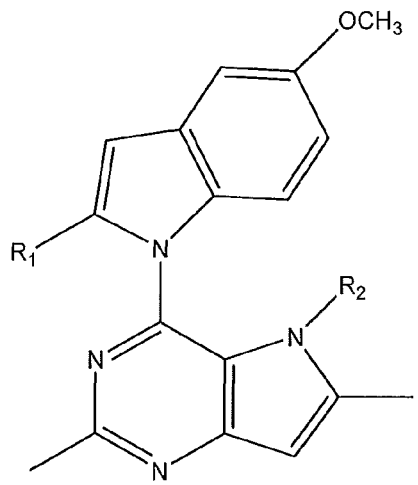
| COMPOSITION NUMBER | $R_1$ | $R_2$ |
|---|---|---|
| 94 | H | H |
| 95 | $CH_3$ | H |
| 96 | H | $CH_3$ |
| 97 | $CH_3$ | $CH_3$ |
Series XIII:
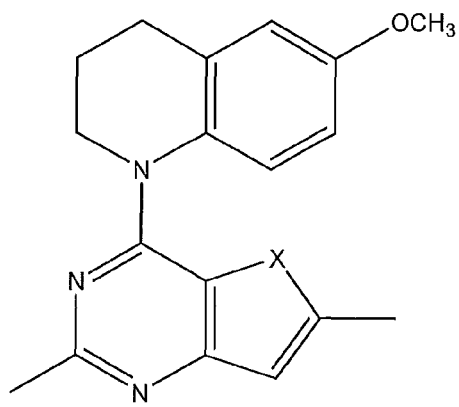
| COMPOSITION NUMBER | X |
|---|---|
| 98 | $NCH_3$ |
| 99 | O |
| 100 | S |
Figure 6

Series XIV:
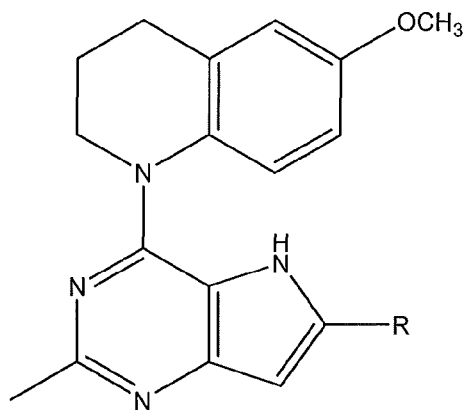
| COMPOSITION NUMBER | R |
|---|---|
| 101 | $CH_2CH_3$ |
| 102 | $(CH_2)_2CH_3$ |
| 103 | $CH(CH_3)_2$ |
Series XVa:
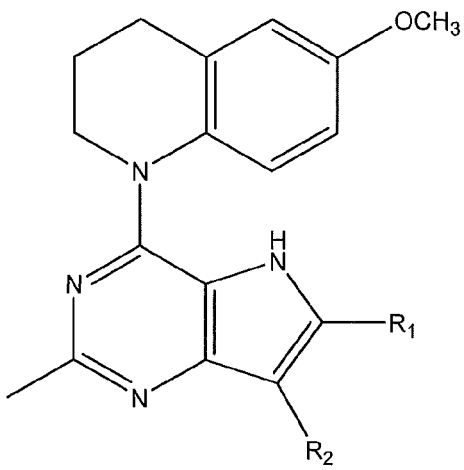
| COMPOSITION NUMBER | $R_1$ | $R_2$ |
|---|---|---|
| 104 ("RP249") | $CH_3$ | H |
| 105 | $CH_3$ | $CH_3$ |
Figure 7

Series XVb:
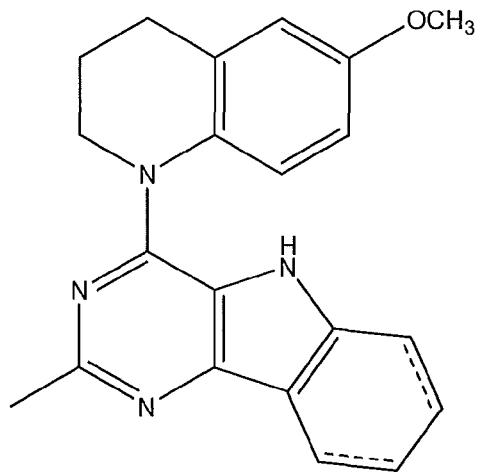
Composition No. 106
Series XVIa:
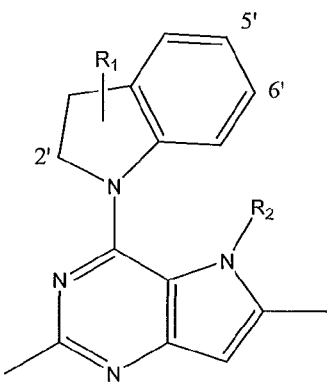
| COMPOSITION NUMBER | $R_1$ | $R_2$ |
|---|---|---|
| 107 | 2'-$CH_3$, 5'-$OCH_3$ | H |
| 108 | 6'-$OCH_3$, 5'-$OCH_3$ | H |
| 109 | 5'-$OCH_2CH_3$ | H |
| 110 | 5'-$OCH_3$ | H |
| 111 | 5'$OCH_3$ | $CH_3$ |
Figure 8

Series XVIb:
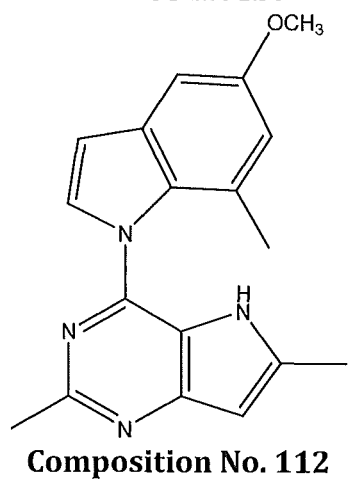
Composition No. 112
Series XVIc:
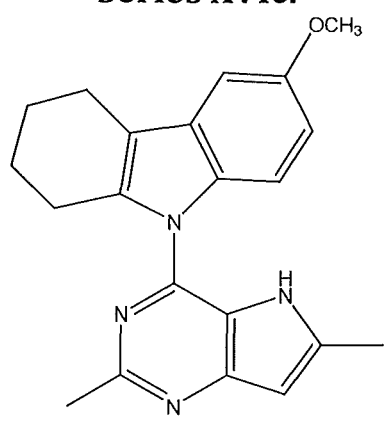
Composition No. 113
Figure 9

Series XVII:
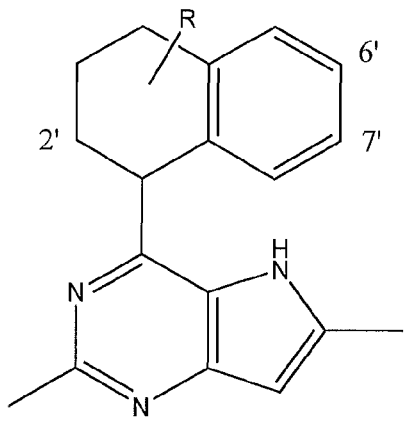
| COMPOSITION NUMBER | R |
|---|---|
| 114 | 2'-CH₃, 6'-OCH₃ |
| 115 | 7'-OCH₃, 6'-OCH₃ |
| 116 | 7'-OH, 6'-OCH₃ |
| 117 | 2'-CH₃, 6'-OH |
| 118 | 6'-OCF₃ |
Series XVIII:
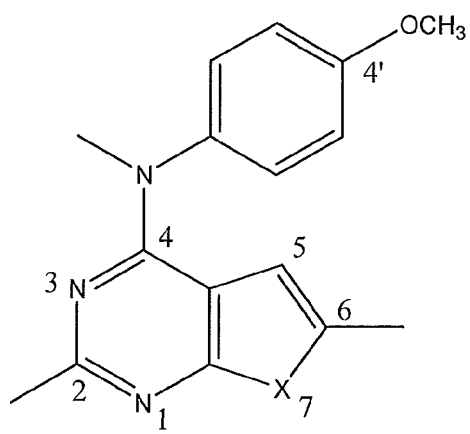
| COMPOSITION NUMBER | X |
|---|---|
| 121 | S |
Figure 10

Series XX:
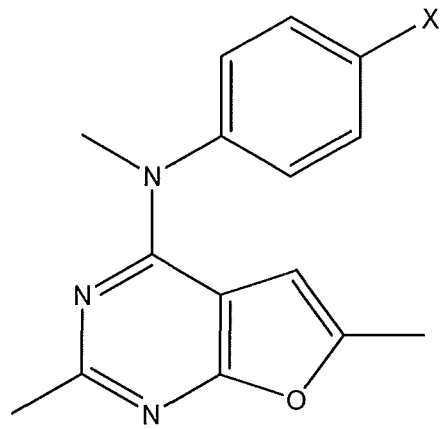
| COMPOSITION NUMBER | X |
|---|---|
| 125 | SCH$_3$ |
Series XXII:
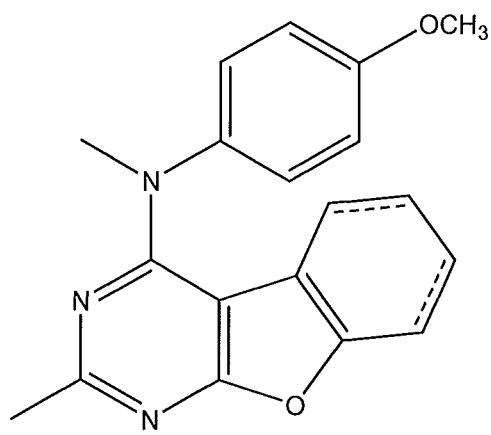
Composition No. 138
Figure 11

Series XXIIIa:
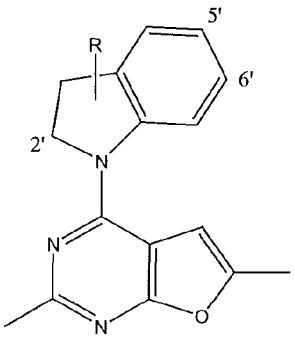
| COMPOSITION NUMBER | R |
| --- | --- |
| 139 | 2'-CH$_3$, 5'-OCH$_3$ |
| 140 | 6'-OCH$_3$, 5'-OCH$_3$ |
| 141 | 5'-OCH$_2$CH$_3$ |
Series XXIIIb:
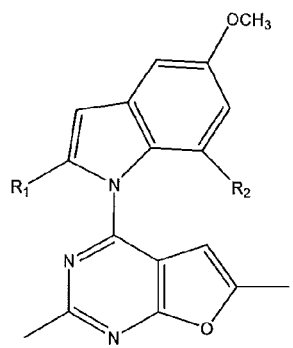
| COMPOSITION NUMBER | R$_1$ | R$_2$ |
| --- | --- | --- |
| 142 | H | H |
| 143 | CH$_3$ | H |
| 144 | H | CH$_3$ |
Series XXIIIc:
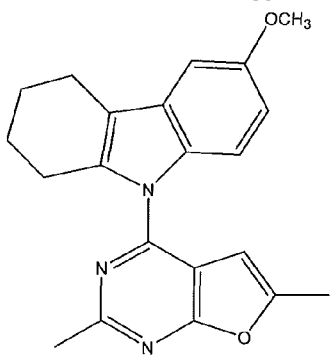
Composition No. 145
Figure 12

Series XXIV:

| COMPOSITION NUMBER | R |
|---|---|
| 146 | 2'-CH$_3$, 6'-OCH$_3$ |
| 147 | 7'-OCH$_3$, 6'-OCH$_3$ |
| 148 | 7'-OH, 6'-OCH$_3$ |
| 149 | 2'-CH$_3$, 6'-OH |
| 150 | 6'-OCF$_3$ |

National Cancer Institute Developmental Therapeutics Program
In-Vitro Testing Results

| NSC : D - 754268 / 1 | Experiment ID : 1009NS24 | Test Type : 08 | Units : Molar |
|---|---|---|---|
| Composition No. 104 | | QNS : | MC : |
| COMI : RP/AG/159-249 (98554) | Stain Reagent : SRB Dual-Pass Related | SSPL : 0D4H | |

| Panel/Cell Line | Time Zero | Ctrl | Mean Optical Densities -8.0 | -7.0 | -6.0 | -5.0 | -4.0 | Percent Growth -8.0 | -7.0 | -6.0 | -5.0 | -4.0 | GI50 | TGI | LC50 |
|---|---|---|---|---|---|---|---|---|---|---|---|---|---|---|---|
| Leukemia | | | | | | | | | | | | | | | |
| CCRF-CEM | 0.218 | 1.011 | 0.976 | 0.314 | 0.296 | 0.293 | 0.244 | 95 | 12 | 10 | 9 | 3 | 3.61E-8 | > 1.00E-4 | > 1.00E-4 |
| HL-60(TB) | 0.654 | 2.252 | 2.237 | 0.536 | 0.510 | 0.506 | 0.522 | 99 | -18 | -22 | -23 | -20 | 2.62E-8 | 7.01E-6 | > 1.00E-4 |
| K-562 | 0.131 | 1.028 | 1.072 | 0.276 | 0.222 | 0.190 | 0.161 | 105 | 16 | 10 | 7 | 3 | 4.15E-8 | > 1.00E-4 | > 1.00E-4 |
| MOLT-4 | 0.437 | 1.708 | 1.800 | 1.066 | 0.673 | 0.660 | 0.630 | 107 | 50 | 19 | 18 | 15 | 9.03E-8 | > 1.00E-4 | > 1.00E-4 |
| RPMI-8226 | 0.500 | 2.211 | 2.131 | 0.906 | 1.063 | 0.982 | 0.895 | 95 | 24 | 33 | 28 | 11 | 4.29E-8 | > 1.00E-4 | > 1.00E-4 |
| SR | 0.352 | 1.873 | 1.773 | 0.426 | 0.341 | 0.315 | 0.369 | 93 | 5 | -3 | -11 | 1 | 3.09E-8 | | > 1.00E-4 |
| Non-Small Cell Lung Cancer | | | | | | | | | | | | | | | |
| A549/ATCC | 0.362 | 1.404 | 1.399 | 0.543 | 0.416 | 0.437 | 0.341 | 100 | 17 | 5 | 7 | -6 | 4.01E-8 | 3.58E-5 | > 1.00E-4 |
| EKVX | 0.629 | 1.368 | 1.366 | 0.998 | 0.837 | 0.964 | 0.774 | 100 | 50 | 28 | 45 | 20 | 9.96E-8 | > 1.00E-4 | > 1.00E-4 |
| HOP-62 | 0.485 | 1.170 | 1.134 | 0.667 | 0.637 | 0.598 | 0.470 | 95 | 27 | 22 | 16 | -3 | 4.53E-8 | 6.87E-5 | > 1.00E-4 |
| HOP-92 | 0.808 | 1.526 | 1.463 | 1.308 | 1.324 | 1.121 | 1.048 | 91 | 70 | 72 | 44 | 33 | 5.05E-6 | > 1.00E-4 | > 1.00E-4 |
| NCI-H226 | 0.595 | 1.257 | 1.180 | 0.886 | 0.694 | 0.671 | 0.622 | 89 | 46 | 19 | 15 | 8 | 6.23E-8 | > 1.00E-4 | > 1.00E-4 |
| NCI-H23 | 0.535 | 1.643 | 1.676 | 0.997 | 0.835 | 0.736 | 0.641 | 103 | 41 | 27 | 18 | 10 | 7.10E-8 | > 1.00E-4 | > 1.00E-4 |
| NCI-H322M | 0.679 | 1.151 | 1.102 | 0.813 | 0.774 | 0.805 | 0.751 | 90 | 28 | 20 | 27 | 15 | 4.42E-8 | > 1.00E-4 | > 1.00E-4 |
| NCI-H460 | 0.330 | 2.330 | 2.444 | 0.476 | 0.356 | 0.327 | 0.267 | 106 | 7 | 1 | -1 | -19 | 3.69E-8 | 3.04E-6 | > 1.00E-4 |
| Colon Cancer | | | | | | | | | | | | | | | |
| COLO 205 | 0.241 | 0.915 | 0.930 | 0.200 | 0.076 | 0.022 | 0.012 | 102 | -17 | -68 | -91 | -95 | 2.74E-8 | 7.20E-8 | 4.38E-7 |
| HCC-2998 | 0.656 | 2.506 | 2.424 | 1.522 | 0.849 | 0.690 | 0.552 | 96 | 47 | 10 | 2 | -18 | 8.60E-8 | 1.27E-5 | > 1.00E-4 |
| HCT-116 | 0.175 | 1.643 | 1.627 | 0.417 | 0.247 | 0.210 | 0.236 | 99 | 16 | 5 | 2 | 4 | 3.92E-8 | > 1.00E-4 | > 1.00E-4 |
| HCT-15 | 0.199 | 1.160 | 1.130 | 0.396 | 0.314 | 0.242 | 0.230 | 99 | 21 | 12 | 4 | 3 | 4.21E-8 | > 1.00E-4 | > 1.00E-4 |
| HT29 | 0.167 | 1.068 | 1.118 | 0.252 | 0.219 | 0.191 | 0.180 | 105 | 9 | 6 | 3 | 1 | 3.77E-8 | > 1.00E-4 | > 1.00E-4 |
| KM12 | 0.218 | 0.926 | 0.924 | 0.286 | 0.161 | 0.121 | 0.067 | 100 | 10 | -26 | -45 | -69 | 3.56E-8 | 1.84E-7 | 1.64E-6 |
| SW-620 | 0.271 | 1.433 | 1.403 | 0.484 | 0.487 | 0.448 | 0.432 | 97 | 18 | 19 | 15 | 14 | 3.96E-8 | > 1.00E-4 | > 1.00E-4 |
| CNS Cancer | | | | | | | | | | | | | | | |
| SF-268 | 0.489 | 1.350 | 1.281 | 0.827 | 0.668 | 0.654 | 0.474 | 92 | 39 | 21 | 19 | -3 | 6.26E-8 | 7.21E-5 | > 1.00E-4 |
| SF-295 | 0.830 | 1.539 | 1.379 | 0.439 | 0.388 | 0.369 | 0.324 | 77 | -47 | -53 | -63 | -61 | 1.66E-8 | 4.19E-8 | 2.86E-7 |
| SF-539 | 0.550 | 1.405 | 1.374 | 0.460 | 0.460 | 0.478 | 0.432 | 96 | -10 | -11 | -13 | -22 | 2.54E-8 | 6.93E-8 | > 1.00E-4 |
| SNB-19 | 0.446 | 1.393 | 1.368 | 0.730 | 0.752 | 0.677 | 0.674 | 97 | 30 | 32 | 24 | 24 | 5.03E-8 | > 1.00E-4 | > 1.00E-4 |
| SNB-75 | 0.567 | 1.133 | 1.067 | 0.693 | 0.811 | 0.697 | 0.587 | 88 | 22 | 43 | 23 | 4 | 3.80E-8 | > 1.00E-4 | > 1.00E-4 |
| U251 | 0.232 | 0.988 | 0.966 | 0.374 | 0.317 | 0.291 | 0.273 | 97 | 19 | 11 | 8 | 5 | 3.99E-8 | > 1.00E-4 | > 1.00E-4 |
| Melanoma | | | | | | | | | | | | | | | |
| LOX IMVI | 0.251 | 1.851 | 1.787 | 0.932 | 0.576 | 0.503 | 0.379 | 96 | 43 | 20 | 16 | 8 | 7.25E-8 | > 1.00E-4 | > 1.00E-4 |
| MALME-3M | 0.679 | 1.142 | 1.075 | 0.701 | 0.798 | 0.827 | 0.760 | 86 | 24 | 26 | 32 | 18 | 3.80E-8 | > 1.00E-4 | > 1.00E-4 |
| M14 | 0.323 | 1.447 | 1.360 | 0.344 | 0.396 | 0.402 | 0.353 | 92 | 2 | 6 | 7 | 3 | 2.94E-8 | > 1.00E-4 | > 1.00E-4 |
| MDA-MB-435 | 0.460 | 1.516 | 1.396 | 0.108 | 0.107 | 0.110 | 0.241 | 88 | -78 | -78 | -77 | -50 | 1.70E-8 | 3.41E-8 | |
| SK-MEL-2 | 0.616 | 1.055 | 1.042 | 0.827 | 0.887 | 0.903 | 0.747 | 98 | 58 | 69 | 72 | 43 | 5.55E-6 | > 1.00E-4 | > 1.00E-4 |
| SK-MEL-28 | 0.458 | 1.183 | 1.120 | 0.778 | 0.818 | 0.808 | 0.709 | 91 | 44 | 50 | 48 | 34 | 7.49E-8 | > 1.00E-4 | > 1.00E-4 |
| SK-MEL-5 | 0.436 | 2.853 | 2.699 | 1.080 | 0.277 | 0.196 | 0.187 | 97 | 29 | -36 | -55 | -57 | 4.86E-8 | 2.75E-7 | 6.30E-6 |
| UACC-257 | 0.595 | 1.074 | 1.034 | 0.830 | 0.829 | 0.847 | 0.822 | 92 | 49 | 49 | 53 | 6 | | > 1.00E-4 | > 1.00E-4 |
| UACC-62 | 0.598 | 1.958 | 1.929 | 0.979 | 1.004 | 0.933 | 0.629 | 98 | 28 | 30 | 25 | 2 | 4.84E-8 | > 1.00E-4 | > 1.00E-4 |
| Ovarian Cancer | | | | | | | | | | | | | | | |
| IGROV1 | 0.491 | 1.420 | 1.427 | 0.720 | 0.451 | 0.458 | 0.346 | 101 | 25 | -8 | -7 | -30 | 4.70E-8 | 5.67E-7 | > 1.00E-4 |
| OVCAR-3 | 0.302 | 0.828 | 0.850 | 0.148 | 0.146 | 0.174 | 0.164 | 106 | -51 | -52 | -43 | -46 | 2.27E-8 | 4.73E-8 | |
| OVCAR-4 | 0.450 | 1.108 | 1.083 | 0.820 | 0.779 | 0.680 | 0.560 | 96 | 56 | 50 | 35 | 18 | 9.60E-7 | > 1.00E-4 | > 1.00E-4 |
| OVCAR-5 | 0.434 | 1.061 | 1.037 | 0.667 | 0.651 | 0.638 | 0.540 | 96 | 37 | 35 | 32 | 17 | 6.07E-6 | > 1.00E-4 | > 1.00E-4 |
| OVCAR-8 | 0.597 | 1.924 | 1.902 | 0.903 | 0.688 | 0.677 | 0.590 | 98 | 23 | 7 | 6 | -1 | 4.39E-8 | 6.87E-5 | > 1.00E-4 |
| NCI/ADR-RES | 0.677 | 1.865 | 1.836 | 0.553 | 0.508 | 0.546 | 0.566 | 98 | -4 | -12 | -5 | -4 | 2.94E-8 | 9.09E-8 | > 1.00E-4 |
| SK-OV-3 | 0.562 | 1.386 | 1.373 | 0.820 | 0.677 | 0.535 | 0.509 | 98 | 7 | 2 | -5 | -9 | 3.39E-8 | 1.07E-6 | > 1.00E-4 |
| Renal Cancer | | | | | | | | | | | | | | | |
| 786-0 | 0.562 | 2.096 | 2.030 | 1.155 | 0.905 | 0.819 | 0.699 | 96 | 39 | 22 | 17 | 9 | 6.31E-8 | > 1.00E-4 | > 1.00E-4 |
| A498 | 1.159 | 1.783 | 1.873 | 1.141 | 1.028 | 1.007 | 0.933 | 82 | -2 | -11 | -13 | -20 | 2.43E-8 | 9.57E-8 | > 1.00E-4 |
| ACHN | 0.332 | 1.287 | 1.278 | 0.724 | 0.411 | 0.527 | 0.416 | 99 | 41 | 29 | 20 | 9 | 7.01E-8 | > 1.00E-4 | > 1.00E-4 |
| CAKI-1 | 0.736 | 2.095 | 2.004 | 1.041 | 0.953 | 0.977 | 0.833 | 95 | 23 | 16 | 18 | 7 | 4.23E-8 | > 1.00E-4 | > 1.00E-4 |
| RXF 393 | 0.620 | 1.178 | 1.116 | 0.645 | 0.836 | 0.856 | 0.784 | 89 | 4 | 39 | 42 | 29 | 2.89E-8 | > 1.00E-4 | > 1.00E-4 |
| SN12C | 0.475 | 1.530 | 1.470 | 0.967 | 0.759 | 0.706 | 0.640 | 94 | 47 | 27 | 22 | 16 | 8.49E-8 | > 1.00E-4 | > 1.00E-4 |
| TK-10 | 0.433 | 1.034 | 1.015 | 0.708 | 0.774 | 0.802 | 0.661 | 97 | 46 | 57 | 61 | 38 | | > 1.00E-4 | > 1.00E-4 |
| UO-31 | 0.590 | 1.118 | 1.053 | 0.782 | 0.734 | 0.607 | 0.409 | 88 | 36 | 27 | 3 | -31 | 5.43E-8 | 1.24E-5 | > 1.00E-4 |
| Prostate Cancer | | | | | | | | | | | | | | | |
| PC-3 | 0.487 | 1.632 | 1.591 | 0.835 | 0.805 | 0.788 | 0.734 | 96 | 30 | 28 | 26 | 22 | 5.04E-8 | > 1.00E-4 | > 1.00E-4 |
| DU-145 | 0.409 | 1.323 | 1.343 | 0.464 | 0.267 | 0.304 | 0.331 | 102 | 6 | -35 | -26 | -19 | 3.49E-8 | 1.40E-7 | > 1.00E-4 |
| Breast Cancer | | | | | | | | | | | | | | | |
| MCF7 | 0.239 | 1.234 | 1.180 | 0.416 | 0.390 | 0.338 | 0.274 | 95 | 18 | 15 | 10 | 4 | 3.80E-8 | > 1.00E-4 | > 1.00E-4 |
| MDA-MB-231/ATCC | 0.661 | 1.324 | 1.391 | 1.004 | 0.687 | 0.723 | 0.676 | 110 | 50 | 1 | 6 | -1 | 1.01E-7 | 7.74E-5 | > 1.00E-4 |
| HS 578T | 0.533 | 0.933 | 0.929 | 0.517 | 0.530 | 0.515 | 0.479 | 99 | -3 | 1 | -3 | -10 | 3.02E-8 | | > 1.00E-4 |
| BT-549 | 0.732 | 1.652 | 1.602 | 1.271 | 1.038 | 1.080 | 0.967 | 95 | 59 | 33 | 38 | 25 | 2.18E-7 | > 1.00E-4 | > 1.00E-4 |
| T-47D | 0.543 | 1.191 | 1.192 | 0.826 | 0.823 | 0.868 | 0.674 | 100 | 44 | 43 | 49 | 20 | 7.74E-8 | > 1.00E-4 | > 1.00E-4 |
| MDA-MB-468 | 0.470 | 1.220 | 1.170 | 0.357 | 0.303 | 0.282 | 0.433 | 93 | -24 | -36 | -40 | -8 | 2.34E-8 | 6.23E-8 | > 1.00E-4 |

Figure 14

| Compound | Inhibition of tubulin assembly IC$_{50}$ (μM) ± SD | Inhibition of colchicine binding % Inhibition ± SD | |
| --- | --- | --- | --- |
| | | 5 μM inhibitor | 1 μM inhibitor |
| CSA4 | 1.2 ± 0.01 | 98 ± 0.3 | 84 ± 3 |
| RP/AG/159-249 | 1.2 ± 0.007 | 76 ± 0.5 | |

Figure 15

| Composition | MW | EGFR Kinase Inhibitor μM | Flk-1 (VEGR2) Kinase Inhibition μM | Flt-1 Kinase Inhibition | PDGFR Kinase Inhibition μM | A431 Cytotoxicity μM |
|---|---|---|---|---|---|---|
| RP/AG/159-249 (Composition No. 104) | 362.856 | 20.2sd3.8 | 30.6sd4.5 | >300 | 82.3sd.10.3 | 10.1sd1.8 |
| RP/AG/159-248 (Composition No. 106) | 386.277 | 29.3sd4.1 | 55.2sd8.3 | >300 | 110.2sd18.0 | 183.2sd19 |
| Positive Controls | | | | | | |
| PD153035 | | 0.21sd0.002 | 124.7sd18.2 | | 12.2sd1.9 | |
| PD168393 | | 0.13 | | | | |
| SU5416 | | | 12.9 | | | |
| Doxirubicin (DOX) | | | | | | 1.35sd0.03 |
| Cisplatin | | | | | | 16.2sd3.1 |
| VEGF Kinase Inhibitor II | | | | 17.6sd3.1 | | |
| Sunitinib | | 172.1sd19.4 | 18.9sd2.7 | | 83.1sd10.1 | |
| Erlotinib | | 1.2sd0.2 | 124.7sd18.2 | | 12.2sd1.9 | |
| DMBI | | | | | 3.75 | |

Figure 16

Scheme A
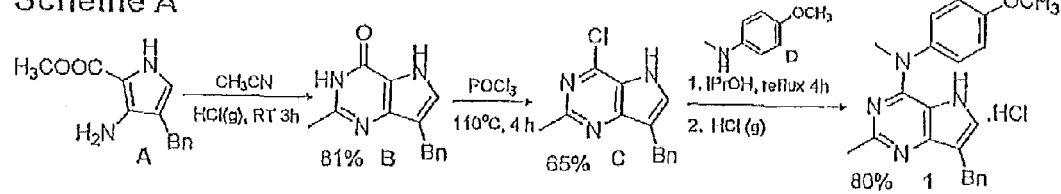
Scheme B (Synthesis of RP 249)
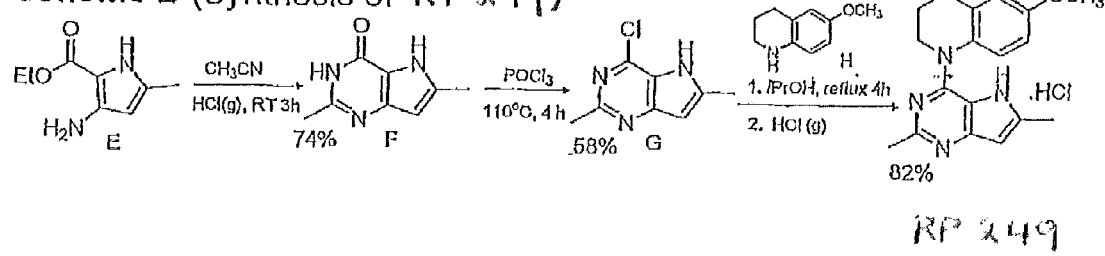
Scheme C
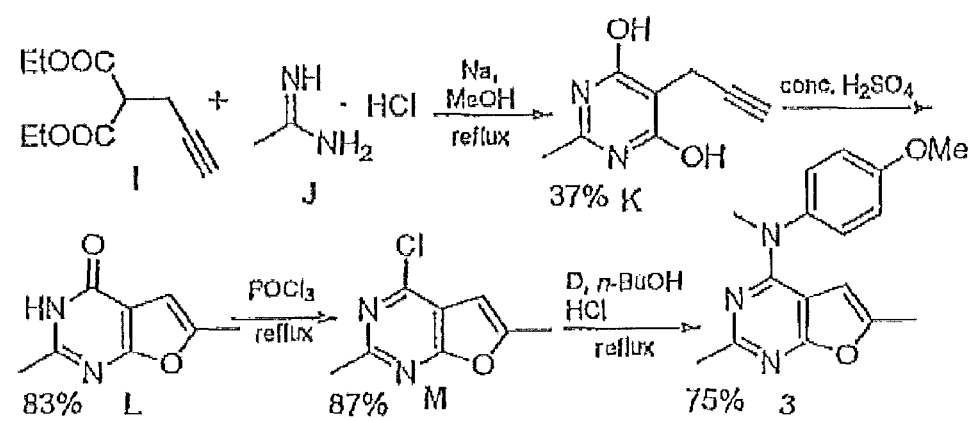
Figure 18

| COMPOUND | | kinase inhibition | | | A431 cytotoxicity |
|---|---|---|---|---|---|
| | | EGFR | VEGFR2 | PDGFR | |
| | | (μM) | (μM) | (μM) | (μM) |
| 106. HCl | [structure] | 29.3±4.1 | 55.2±8.3 | 110.2±18.0 | 183.2±19 |
| PD153035 | | 0.21±0.002 | 124.7±18.2 | 12.2±1.9 | |
| SU5416 | | | 12.9 | | |
| DOX | | | | | 1.35±0.03 |
| cisplatin | | | | | 16.2±3.1 |
| sunitinib | | 172.1±19.4 | 18.9±2.7 | 83.1±10.1 | |
| erlotinib | | 1.2±0.2 | 124.7±18.2 | 12.2±1.9 | |
| DMBI | | | | 3.75 | |

Figure 19

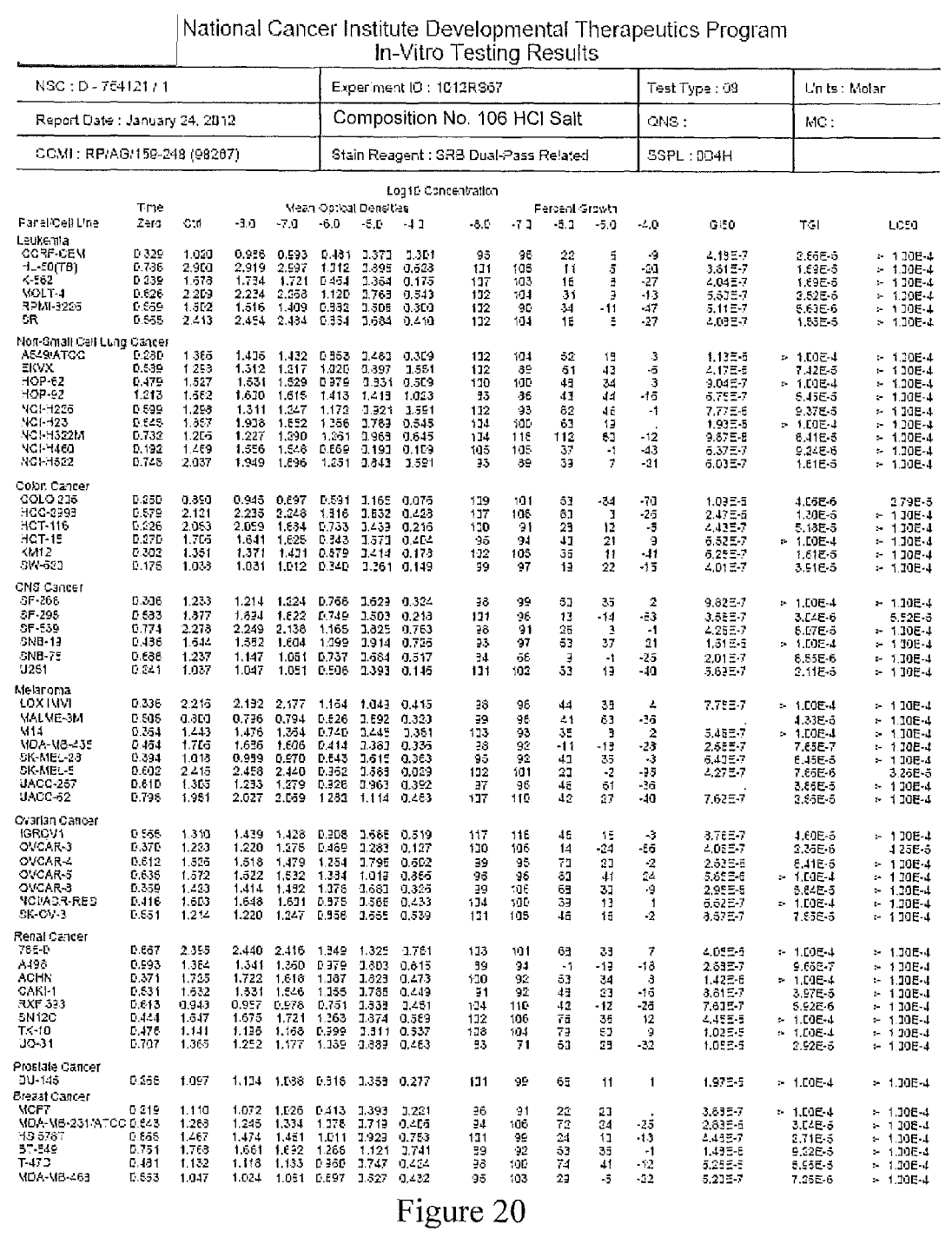

| National Cancer Institute Developmental Therapeutics Program In-Vitro Testing Results | | | |
|---|---|---|---|
| NSC : D - 764121 / 1 | Experiment ID : 1012RS67 | Test Type : 08 | Units : Molar |
| Report Date : January 24, 2012 | Composition No. 106 HCl Salt | ONS : | MC : |
| CCMI : RP/AG/159-248 (98267) | Stain Reagent : SRB Dual-Pass Related | SSPL : 0D4H | |

Figure 20

| National Cancer Institute Developmental Therapeutics Program Dose Response Curves | NSC: D - 754121 / 1 | SSPL: 0D4H | EXP. ID: 1012RS67 |
|---|---|---|---|
| | Report Date: January 24, 2012 | Composition No. 106 HCl Salt | |
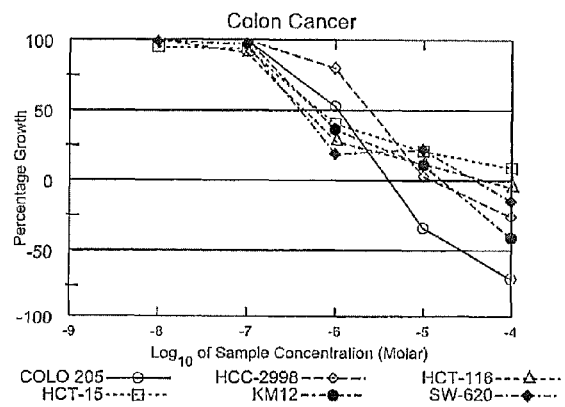
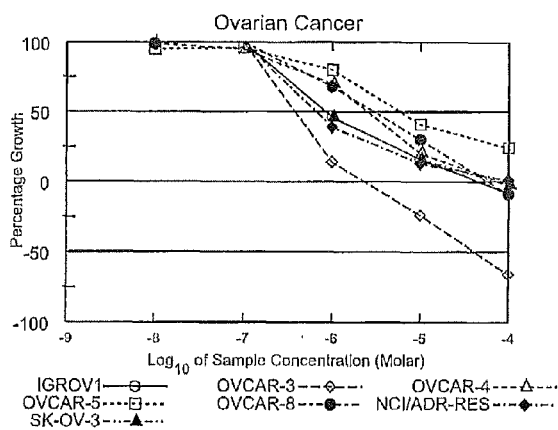
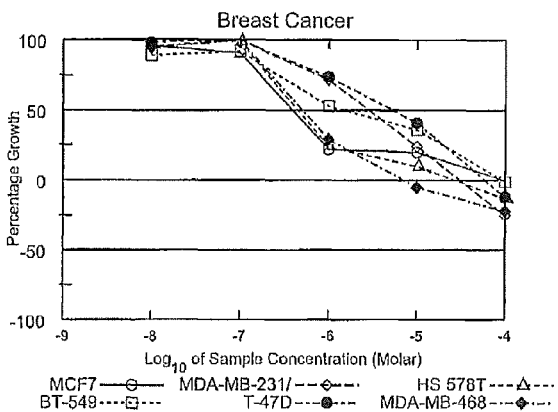
Figure 22c Scheme A
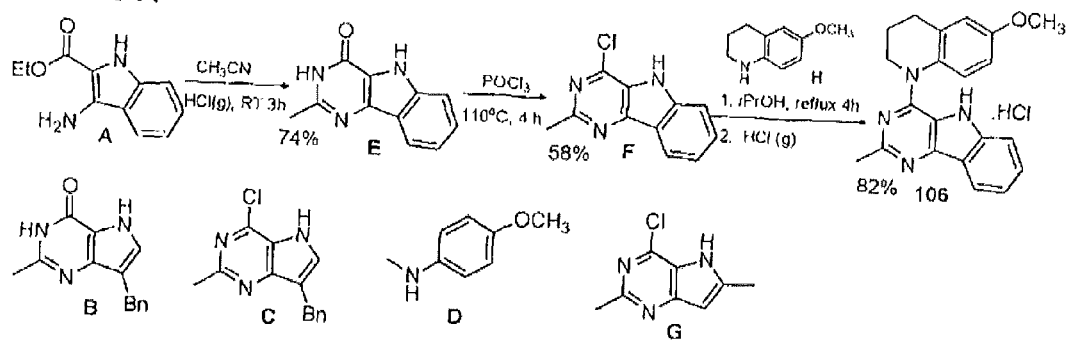
Scheme C
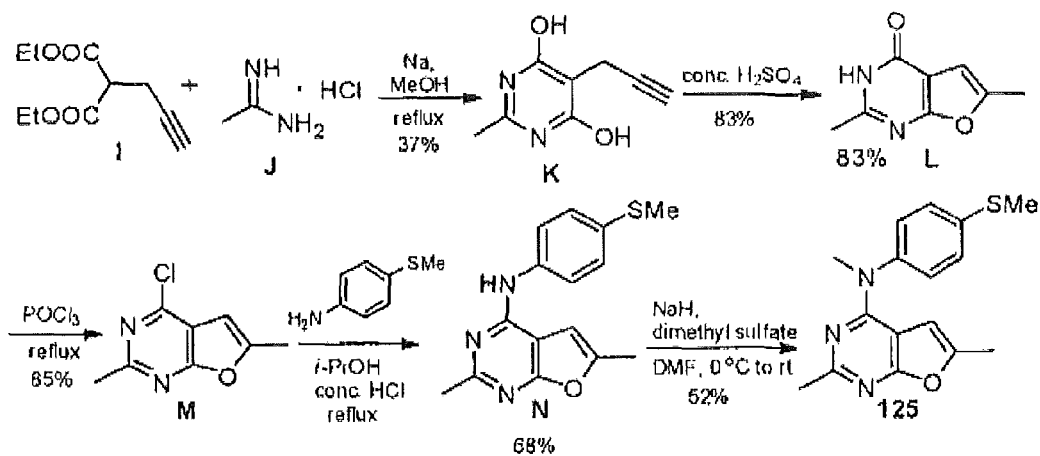
Figure 24

Scheme 1: General method for 4-Chloro displacement
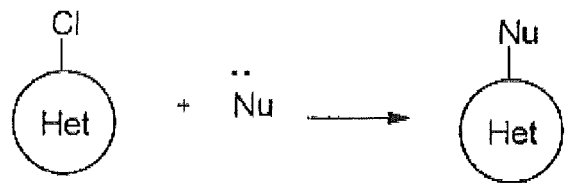
Scheme 2 (Series I)
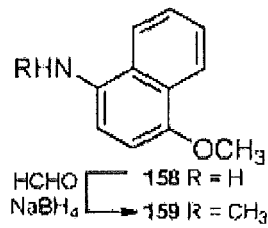
Scheme 3 (Series I)
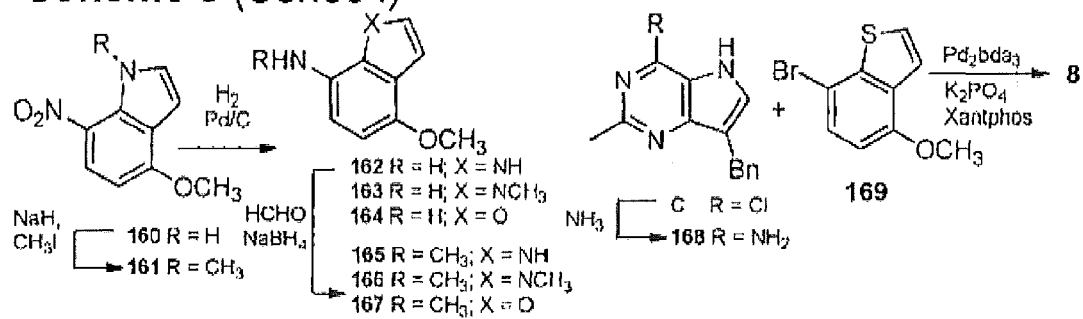
Figure 25

Scheme 5 (Series II, III)
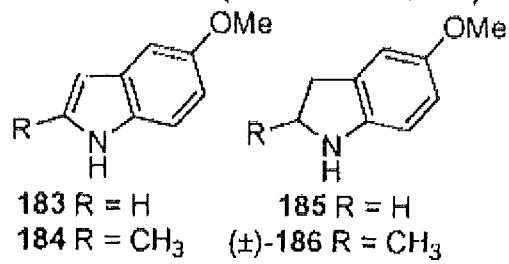
183 R = H
184 R = CH₃
185 R = H
(±)-186 R = CH₃
Scheme 6 (Series III)
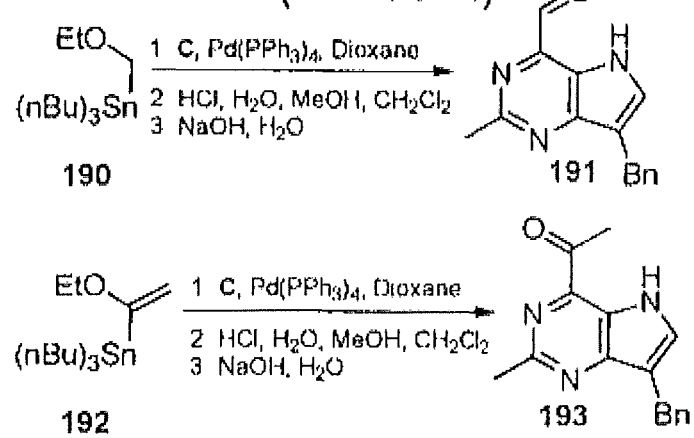
Scheme 7 (Series IV)
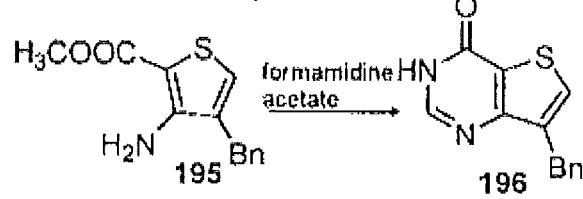
Figure 26

Scheme 12
(Series VII)
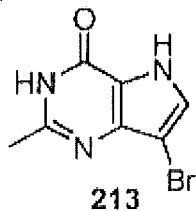
213
Scheme 13 (Series VIII)
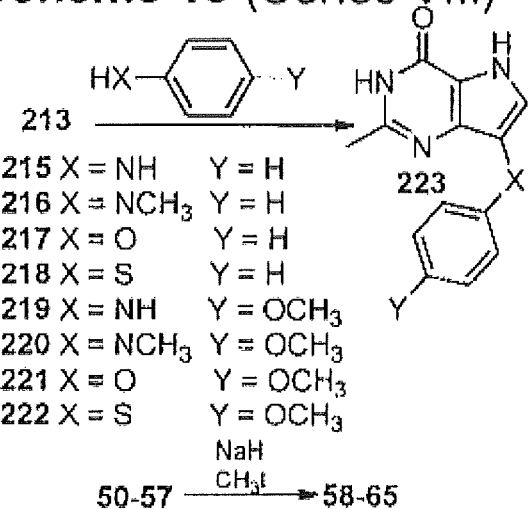
| 215 X = NH | Y = H |
| 216 X = NCH₃ | Y = H |
| 217 X = O | Y = H |
| 218 X = S | Y = H |
| 219 X = NH | Y = OCH₃ |
| 220 X = NCH₃ | Y = OCH₃ |
| 221 X = O | Y = OCH₃ |
| 222 X = S | Y = OCH₃ |
50-57 →(NaH, CH₃I)→ 58-65
Figure 27

Scheme 15 (Series X)
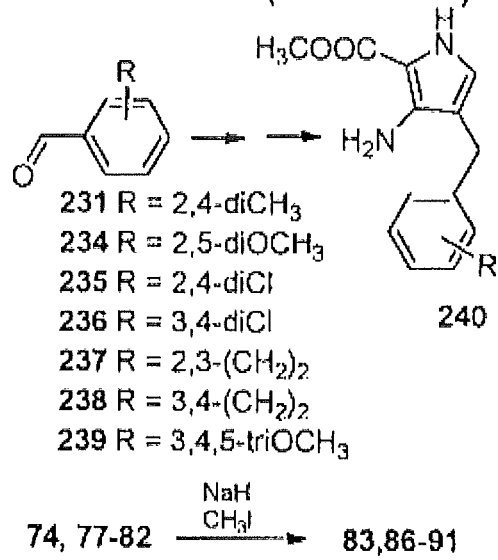
231 R = 2,4-diCH₃
234 R = 2,5-diOCH₃
235 R = 2,4-diCl
236 R = 3,4-diCl
237 R = 2,3-(CH₂)₂
238 R = 3,4-(CH₂)₂
239 R = 3,4,5-triOCH₃
74, 77-82 $\xrightarrow{\text{NaH} \atop \text{CH}_3\text{I}}$ 83, 86-91
Scheme 16 (Series XI)
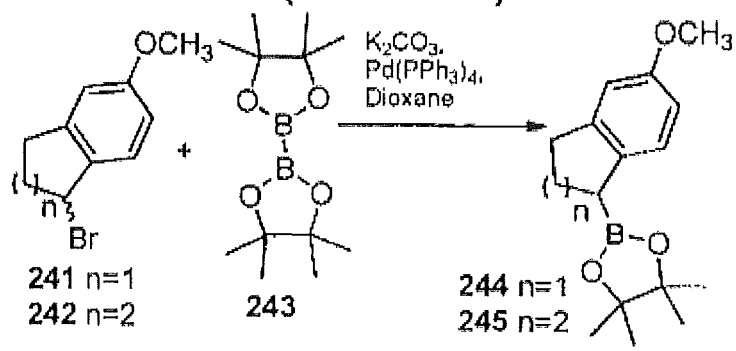
241 n=1
242 n=2
243
244 n=1
245 n=2
Scheme 17 (Series XII)
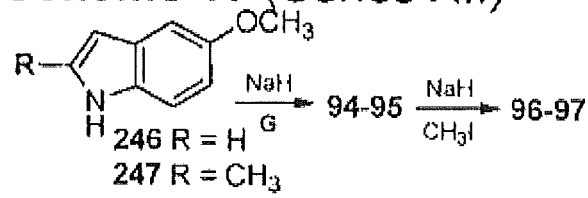
246 R = H
247 R = CH₃
$\xrightarrow{\text{NaH} \atop \text{G}}$ 94-95 $\xrightarrow{\text{NaH} \atop \text{CH}_3\text{I}}$ 96-97
Figure 28

Scheme 18 (Series XIII, XIV)
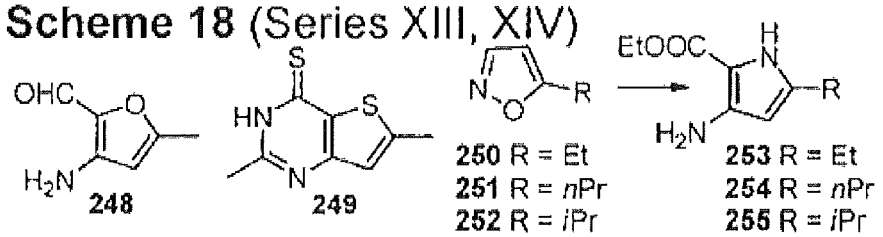
Scheme 19 (Series XV)
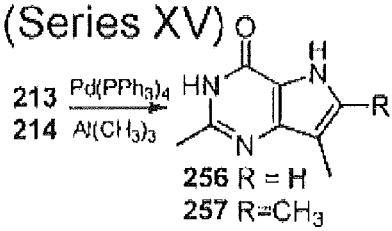
Scheme 20 (Series XV)
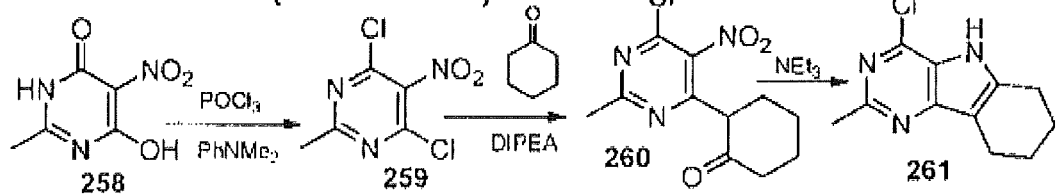
Figure 29

Scheme 21 (Series XVI, XVII, XVIII, XXIII, XXIV)
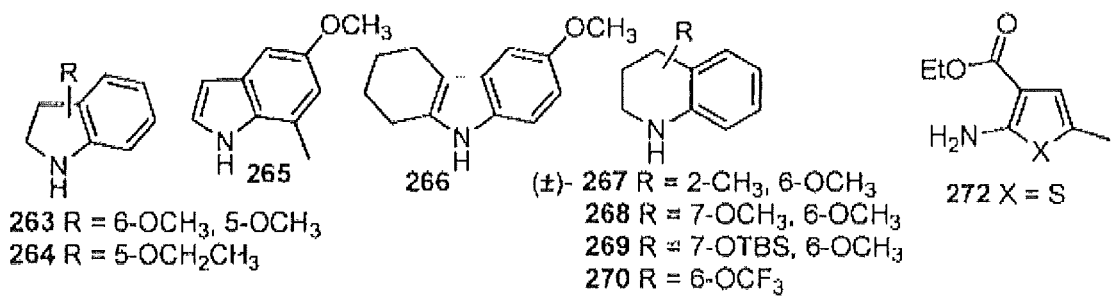
Scheme 22 (Series XIX)
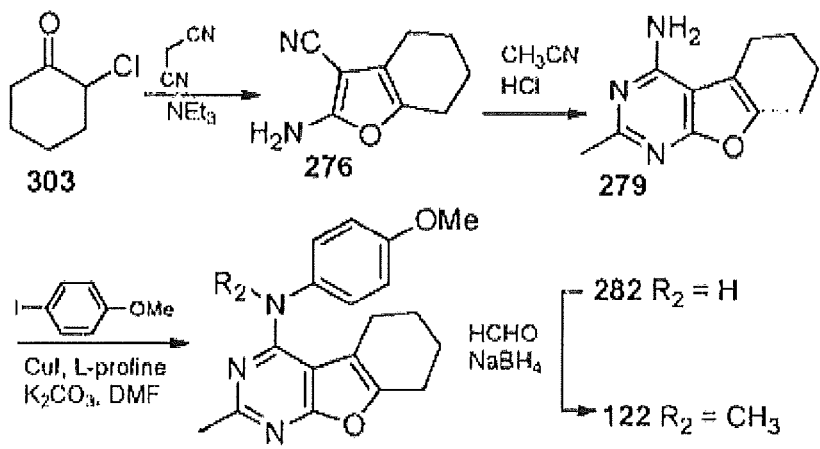
Figure 30

BICYCLIC AND TRICYCLIC PYRIMIDINE TYROSINE KINASE INHIBITORS WITH ANTITUBULIN ACTIVITY AND METHODS OF TREATING A PATIENT

BENEFIT OF PRIOR PATENT APPLICATION

This divisional utility patent application claims the benefit of co-pending U.S. patent application Ser. No. 13/364,930, filed on Feb. 2, 2012, which claims the benefit of U.S. Provisional Patent Application Ser. No. 61/439,470, filed Feb. 4, 2011. The entire contents of U.S. patent application Ser. No. 13/364,930 and U.S. Provisional Patent Application Ser. No. 61/439,470 are incorporated by reference into this divisional utility patent application.

BACKGROUND OF THE INVENTION

1. Field of the Invention

The present invention relates to bicyclic and tricyclic pyrimidine tyrosine kinase inhibitors with antitubulin activity. The compositions of this invention have dual activity of potent vascular endothelial growth factor receptor inhibitory activity along with cytotoxic activity in a single agent. The compositions of this invention may be made into salts that are water soluble for providing orally active antiangiogenic agents. Methods of using these compositions for treating a patient are also provided.

2. Description of the Background Art

Antitubulin agents are some of the most successful cancer chemotherapeutic agents and are clinically used in a variety of cancers. Three distinct classes of antitubulin binding agents have been identified depending on their binding on tubulin.

The taxanes, including paclitaxel and docetaxel, are highly successful agents in cancer chemotherapy, both as monotherapy and in combination in solid tumors, particularly in breast, lung, ovarian, head and neck, and bladder cancers, among several others. The binding site of the taxanes (including epothilones) lies on the inside surface of the β-subunit of the alpha beta (αβ)-heterodimer that make up the microtubule. These compounds increase microtubule polymerization and are referred to as microtubule stabilizing agents.

The second class of antitubulin binding agents is the *Vinca* alkaloids, including vincristine, vinblastine, vinorelbine, and vindesine. These compounds are clinically used in leukemias, lymphomas, small cell lung cancer, and other cancers, and also bind to the β-subunit of tubulin, but at a distinctly different site than the taxanes. Further, unlike the taxanes, the Vincas are microtubule polymerization inhibitors.

The colchicine site binding agents comprise a third class of antitubulin binding agents which includes colchicine and a variety of small molecules that bind to β-tubulin at the interface with α-tubulin. The colchicine binding agents inhibit the polymerization of tubulin. Combretastatins (CA) are a class of colchicine site binding agents of which the water soluble analog CA4P (Zybrestat7) has been approved by the FDA for metastatic anaplastic thyroid cancer (ATC) and ovarian cancer, and has been accorded fast track status for other types of cancer. Several colchicine site binding agents are currently in clinical trials, and the FDA approval of CA4P has established the viability of colchicine site binding agents for the treatment of cancer.

Though antimitotic agents have unprecedented success in the chemotherapy of cancer both as monotherapy and in combination, failure rate of cancer chemotherapy with antimitotics is high. This failure is very often due to multidrug resistance (MDR) that is traced to the overexpression of P-glycoprotein (Pgp) that pumps the chemotherapeutic agent out of the tumor cell. Pgp overexpression has been reported in a number of tumors in the clinical setting and hence attests to its clinical importance, particularly after patients have received chemotherapy. Overexpression of Pgp appears to be more important in clinical tumor resistance than elevation of MRP1 levels. Thus the clinical success of new microtubule targeting drugs will depend, to a significant extent, on the drugs not being subject to Pgp resistance.

βIII-tubulin is an isoform of the β-tubulin to which the taxanes and *Vinca* alkaloids bind. βIII-tubulin plays a major role in clinical resistance to the taxanes and Vincas in lung, breast, ovarian, and gastric tumors, among others. The importance of βIII-tubulin in chemotherapy resistance has been published and is known by those skilled in the art. It has been shown that tumor resistance due to βIII-tubulin can be circumvented with colchicine site binding agents and highlights the critical importance developing new agents that bind to the colchicine site on tubulin as clinically important alternatives to tumors resistant to the taxanes and Vincas.

The compositions of the present invention bind to the colchicine site and are believed to circumvent βIII-tubulin resistance. The recent FDA approval of ixabepilone attests to the need to overcome βIII-tubulin resistance. Clinical evidence implicates both Pgp and βIII-tubulin as the most important mechanisms of treatment failure for the taxanes and Vincas. Thus, there is an urgent need for new drugs that circumvent Pgp and/or βIII-tubulin mediated tumor resistance that would be useful for the large number of patients that either do not respond to or have developed resistance to the taxanes and/or the Vincas. The compounds of the present invention are believed to overcome both resistance mechanisms and fill an unmet need for patients resistant to taxanes and *Vinca* alkaloids.

Poor water solubility has plagued the clinical use of taxanes and is an important drawback of ixabepilone as well. Enormous effort continues to be expended to develop soluble formulations of antimitotics. For example, Abraxane (paclitaxel with albumin) reduces the administration time from 3 hrs (for cremophore solvent) to about 1 hour. However, water soluble antimitotics are highly coveted. The compositions of the present invention are highly water soluble as their HCl (or other acid) salts and circumvent the solubility issues associated with other antimitotics.

The combination of two or more antimitotics that act at different or overlapping sites on tubulin often results in synergistic or additive effects. Discodermolide and paclitaxel, vinblastine and paclitaxel, the colchicine analog Cl-980 and docetaxel, paclitaxel plus vinorelbine or docetaxel plus vinorelbine and estramastine with either vinblastine or paxlitaxe are all superior in combination than either drug alone. CA4P, the colchicine site binding agent, is in multiple clinical trials with paclitaxel and the *Vinca* alkaloids, as is a derivative of CA4P termed AVE8063 (clinicaltrials.gov) (Omrabulin). Thus, analogs that act at the colchicine site as distinct from the taxane or *Vinca* site are highly desirable to use as monotherapy and in particular in combination chemotherapy with other antimitotics. The compositions of the present invention are believed to act at the colchicine site.

Angiogenesis is the formation of new blood vessels from preexisting ones. Angiogenesis occurs in adults during wound healing, menstrual cycle, and during pregnancy.

Except for these instances, normal adults do not need angiogenesis. Tumor cells, once beyond the 1-2 mm size, are in a state of angiogenesis to provide nutrients needed to grow as well as to metastasize. Angiogenesis is thus a critical factor in the development and metastasis of a variety of tumor types and is an important hallmark of malignant disease. The principal mediator of angiogenesis is vascular endothelial growth factor (VEGF) and its receptor VEGFR2. Other growth factors, such as platelet-derived growth factor (PDGF), are also involved in angiogenesis. Antiangiogenic agents (AA) that inhibit tumor growth defined a new paradigm for cancer treatment. Bevacizumab, an anti-VEGF antibody and the first FDA approved AA significantly increases overall survival (OS) or progression free survival (PFS) of patients with metastatic colorectal cancer, non-small cell lung cancer, and breast cancer in combination with conventional chemotherapeutic agents. More recently, bevacizumab was approved for glioblastoma. Sunitinib and sorafenib, two small molecule VEGFR2 inhibitors (along with other receptor tyrosine kinase (RTK) inhibitors) are approved for advanced renal cell carcinoma, hepatocellular cancer (sorafenib), and gastrointestinal stromal tumor (GIST). Several RTK inhibitors, both approved and in development, including VEGFR2 inhibitors, are currently in clinical trials with the numbers of trials in the several hundred (see clinicaltrials.gov). Although RTK inhibitors in the form of AAs afford a new set of targets for the treatment of a variety of cancers, it is now generally accepted that, with very few exceptions, when used alone, AAs (including multikinase targeting agents) are highly unlikely to afford growth or metastatic control of tumors in the long run in most patients. The heterogeneity of solid tumors and their ability to escape single mechanism targets (like angiogenesis) and the ability to metastasize are two of the reasons for the lack of success of AAs alone. In addition, it is well established that most AAs (with very few exceptions) are cytostatic, in that they arrest tumor growth but do not eradicate the tumor. Thus, it has been determined that the utility of AAs lies in the combination of cytostatic AAs with cytotoxic conventional chemotherapeutic agents and/or radiation to afford the most viable cancer treatment options.

The realization that AAs are cytostatic and that their main utility in treating cancer would be in combination with cytotoxic agents has led to a plethora of combinatorial clinical trials that involve FDA approved AAs as well as those in development, and cytotoxic chemotherapeutic agents (see clinicaltrials.gov). Some of these combinations have been highly successful and were in fact the basis of the approval of bevacizumab, which in combination afforded overall improved or overall and/or progression free survival in colorectal lung and breast cancer. The vast number of clinical trials with AAs and in particular with VEGFR2 inhibitors and antitubulin agents currently ongoing, such as for example, but not limited to, paclitaxel with sorafenib, docetaxal with sorafenib, paclitaxel with sunitinib, docetaxel with sunitinib, paclitaxel with bevacizumab, docetaxel with bevacizumab, paclitaxel with anitinib, docetaxel with axitinib, vincristine with bevacizumab, and vinblastine with bevacizumab, provides strong evidence for the importance of these two types of agents in combination chemotherapy protocols with and without radiation. In addition, a vast number of successful preclinical studies of VEGFR2 inhibitors and antitubulin agents also supports this combination. The two mechanisms that attempt to explain this combination therapy rationale are that chemotherapy when delivered at close regular intervals using relatively low doses with no prolonged drug-free intervals (metronomic therapy) preferentially damages endothelial cells in tumor blood vessels. The antiangiogenic therapy has already destroyed or inhibited much of these endothelial cells, thus the combined effect, like a one-two punch, is amplified on the endothelial cells leading to improved subsequent killing of the tumor cells with the conventional chemotherapeutic agent or radiation. The second mechanism, proposed by Jain and that is widely accepted, is that AAs cause an inhibition of new vessel formation and also prime and kill immature tumor vessels and afford a transient normalization of the remaining tumor vasculature by decrease in macromolecular permeability and consequently the interstitial fluid pressure (IFP) and hypoxia resulting in a transient improvement in blood perfusion to the tumor. It is during this transient window of improved blood perfusion that the cytotoxic agent of the combination is able to penetrate the tumor much more efficiently than in the absence of the AA. Thus, the combination of the cytostatic AA with a cytotoxic agent provides potent additive or synergistic effects that are absent with either drug alone. The details of the preclinical and clinical evidence for normalization of tumor vasculature and the benefit in combination chemotherapy with and without radiation is surfeit in the literature.

There is a need for a composition having dual activity of potent vascular endothelial growth factor receptor inhibitory activity along with cytotoxic activity in a single agent. The present invention provides such single agent compositions.

SUMMARY OF THE INVENTION

The present invention meets the above described need by providing bicyclic and tricyclic pyrimidine compositions that have dual (combined) activity, namely, vascular endothelial growth factor receptor inhibitory activity and antitubulin activity.

The present invention provides a composition of the Formula 5:

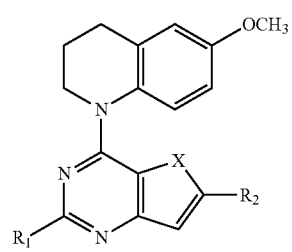

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein X is selected from the group consisting of NH, $NCH_3$, O, and S; and optionally comprising stereochemical conformations thereof; and optionally comprising a pharmaceutically acceptable salt thereof. Preferred embodiments of the compositions embodied by Formula 5 are set forth in Series XIII, FIG. 6, identified by Compositions 98-100, and Series XIV, FIG. 7, identified by Compositions 101-103, and Series XVa, FIG. 7, Composition 104. Composition 104 is also referred to herein as "RP249" and/or "RP/AG/159-249".

The present invention provides a composition of Formula 7:

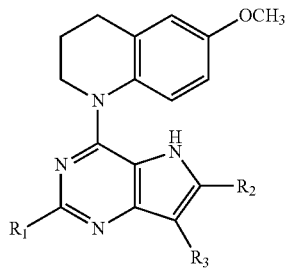

7 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H, a phenyl group, a substituted phenyl group, a benzyl group, a substituted benzyl group, and a straight chain or branched chain alkyl group having from 1 to 10 carbon atoms, and wherein said alkyl group is optionally substituted with one or more of a phenyl group or a substituted phenyl group, or combinations thereof; and wherein each of said substituents of any said substituted group is the same or different and are selected from the group consisting of an electron withdrawing group and an electron donating group, and combinations thereof; and optionally comprising stereochemical conformations thereof; and optionally comprising a pharmaceutically acceptable salt thereof. Preferred embodiments of the compositions embodied by Formula 7 are set forth in Series XIV, Compositions 101-103, FIG. 7, and Series XVa, Compositions 104-105, FIG. 7.

The present invention provides a composition of the Formula 8:

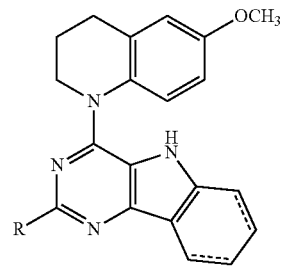

8 comprising wherein R is selected from the group consisting of H, $NH_2$, and a straight chain or branched chain alkyl group having from 1 to 10 carbon atoms; and optionally comprising stereochemical conformations thereof; and optionally comprising a pharmaceutically acceptable salt thereof. Preferred embodiments of the composition embodied by Formula 8 is set forth in Series XVb, FIG. 8, identified by Composition 106. The HCl salt of Composition 106 is also referred to herein as "RP248" and/or "RP/AG/159-248". It will be appreciated that the lower far right ring of the chemical structure set forth in Formula 8 (and in Formula 21 herein) may be completely unsaturated, partially unsaturated, or partially saturated as indicated by the broken double lines in the ring.

The present invention provides a composition of the Formula 9:

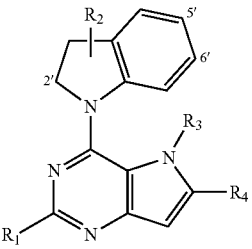

9 comprising wherein $R_1$ is selected from the group consisting of H, $NH_2$, and a straight chain or branched chain alkyl group having from 1 to 10 carbon atoms; and wherein $R_2$ is selected from the group consisting of (a) 2'-$CH_3$, 5'-$OCH_3$, (b) 6'-$OCH_3$, 5'-$OCH_3$, (c) 5'-$OCH_2CH_3$, and (d) 5'-$OCH_3$; and wherein $R_3$ is selected from the group consisting of H and a straight chain or branched chain alkyl group having from 1 to 10 carbon atoms; and wherein $R_4$ is selected from the group consisting of H and a straight chain or branched chain alkyl group having from 1 to 10 carbon atoms; and optionally comprising stereochemical conformations thereof; and optionally comprising a pharmaceutically acceptable salt thereof. Preferred embodiments of the compositions embodied by Formula 9 are set forth in Series XVIa, FIG. 8, identified by Compositions 107-111. It will be appreciated that $R_2$ may be positioned at one of the 2', 5', and 6' positions of one of the two upper rings, and that R2 may be preferably positioned at one or more (multiple) locations of one or both of the two upper rings at positions 2', 5', and 6', and combinations thereof.

The present invention provides a composition of Formula 17:

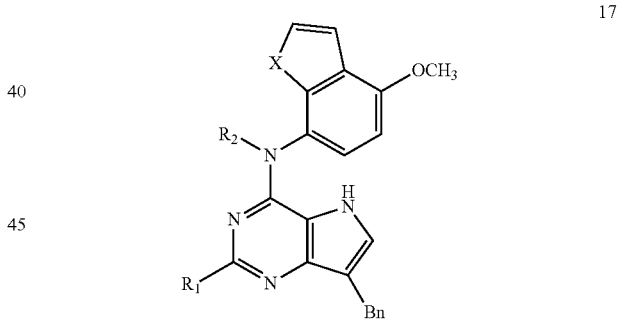

17 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein X is selected from the group consisting of (a) CH=CH, (b) NH, (c) $NCH_3$, (d) O, and (e) S; wherein Bn is selected from the group consisting of H, a phenyl group, a substituted phenyl group, a benzyl group, a substituted benzyl group, and a straight chain or branched chain alkyl group having from 1 to 10 carbon atoms, and wherein said alkyl group is optionally substituted with one or more of a phenyl group or a substituted phenyl group, or combinations thereof; and wherein each of said substituents of any said substituted group is the same or different and are selected from the group consisting of an electron withdrawing group and an electron donating group, and combinations thereof; and optionally comprising stereochemical conformations thereof; and optionally comprising a pharmaceutically acceptable salt thereof. Preferred embodiments of the compositions embodied by Formula 17 are set forth in Series I, FIG. 1, identified by Compositions 4-8.

The present invention provides a composition of Formula 1:

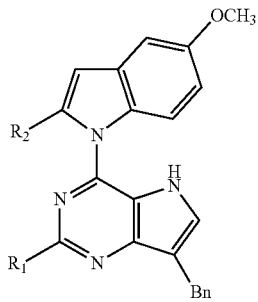

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; wherein Bn is selected from the group consisting of H, a phenyl group, a substituted phenyl group, a benzyl group, a substituted benzyl group, and a straight chain or branched chain alkyl group having from 1 to 10 carbon atoms, and wherein said alkyl group is optionally substituted with one or more of a phenyl group or a substituted phenyl group, or combinations thereof; and wherein each of said substituents of any said substituted group is the same or different and are selected from the group consisting of an electron withdrawing group and an electron donating group, and combinations thereof; and optionally comprising stereochemical conformations thereof; and optionally comprising a pharmaceutically acceptable salt thereof. Preferred embodiments of the compositions embodied by Formula 1 are set forth in Series IIa, FIG. 1, identified by Compositions 15 and 16.

The present invention provides a composition of Formula 2:

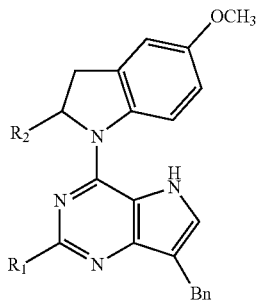

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; wherein Bn is selected from the group consisting of H, a phenyl group, a substituted phenyl group, a benzyl group, a substituted benzyl group, and a straight chain or branched chain alkyl group having from 1 to 10 carbon atoms, and wherein said alkyl group is optionally substituted with one or more of a phenyl group or a substituted phenyl group, or combinations thereof; and wherein each of said substituents of any said substituted group is the same or different and are selected from the group consisting of an electron withdrawing group and an electron donating group, and combinations thereof; and optionally comprising stereochemical conformations thereof; and optionally comprising a pharmaceutically acceptable salt thereof. Preferred embodiments of the compositions embodied by Formula 2 are set forth in Series IIb, FIG. 2, identified by Compositions 17 and 18.

The present invention provides a composition of the Formula 18:

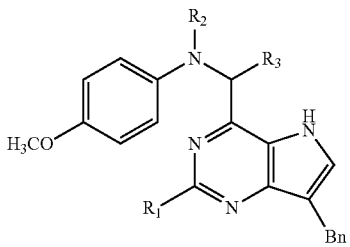

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and wherein Bn is selected from the group consisting of H, a phenyl group, a substituted phenyl group, a benzyl group, a substituted benzyl group, and a straight chain or branched chain alkyl group having from 1 to 10 carbon atoms, and wherein said alkyl group is optionally substituted with one or more of a phenyl group or a substituted phenyl group, or combinations thereof; and wherein each of said substituents of any said substituted group is the same or different and are selected from the group consisting of an electron withdrawing group and an electron donating group, and combinations thereof; and optionally comprising stereochemical conformations thereof; and optionally comprising a pharmaceutically acceptable salt thereof. Preferred embodiments of the compositions embodied by Formula 18 are set forth in Series III, FIG. 2, identified by Compositions 22-24.

The present invention provides a composition of Formula 24:

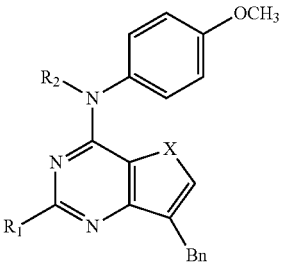

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein X is S; and wherein Bn is selected from the group consisting of H, a phenyl group, a substituted phenyl group, a benzyl group, a substituted benzyl group, and a straight chain or branched chain alkyl group having from 1 to 10 carbon atoms, and wherein said alkyl group is optionally substituted with one or more of a phenyl group or a substituted phenyl group, or combinations thereof; and wherein each of said substituents of any said substituted group is the same or different and are selected from the group consisting of an electron withdrawing group and an electron donating group, and combinations thereof; optionally comprising stereochemical conformations thereof; and optionally comprising a pharmaceutically acceptable salt thereof. A preferred embodiment of the compositions embodied by Formula 24 is set forth in Series IV, FIG. 3, identified by Composition 27.

The present invention provides a composition of the Formula 19:

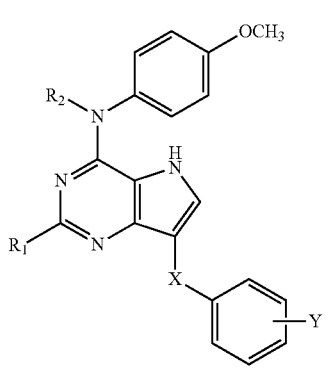

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein X is selected from the group consisting of (a) NH, (b) $NCH_3$, (c) O, and (d) S; and wherein Y is selected from the group consisting of H, $CH_3$, $(CH)_4$, Cl, and $OCH_3$, and wherein Y may be attached at one or more positions of the ring and may be the same or different; and optionally comprising stereochemical conformations thereof; and optionally comprising a pharmaceutically acceptable salt thereof. Preferred embodiments of the compositions embodied by Formula 19 are set forth in Series VIIIa, FIG. 3, identified by Compositions 50-57.

The present invention provides a composition of the Formula 20:

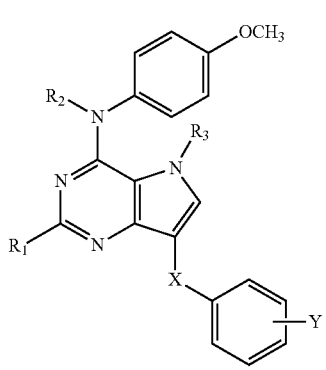

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and wherein X is selected from the group consisting of (a) NH, (b) $NCH_3$, (d) O, and (e) S; and wherein Y is selected from the group consisting of H, $CH_3$, $(CH)_4$, Cl, and $OCH_3$, and wherein Y may be at one or more positions of the ring and may be the same or different; and optionally comprising stereochemical conformations thereof; and optionally comprising a pharmaceutically acceptable salt thereof. Preferred embodiments of the compositions embodied by Formula 20 are set forth in Series VIIIb, FIG. 4, identified by Compositions 58-65.

The present invention provides a composition of Formula 32:

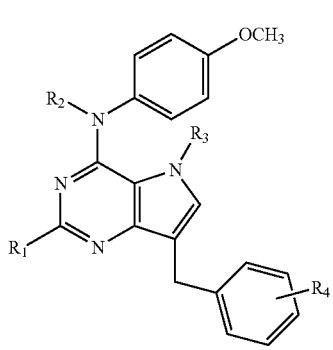

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein R3 is selected from the group consisting of H and a straight or branched chain alkyl group having from 1 to 10 carbon atoms, and wherein $R_4$ is selected from the group consisting of (a) 2',6'-di$CH_3$, (b) 2',5'-di$OCH_3$, (c) 2',4'-diCl, (d) 3',4'-diCl, (e) 2',3'-$(CH)_4$, (f) 3',4'-$(CH)_4$, and (g) 3',4',5'-tri$OCH_3$; and optionally comprising stereochemical conformations thereof; and optionally comprising a pharmaceutically acceptable salt thereof. Preferred embodiments of the compositions embodied by Formula 32 are set forth in Series X(a), FIG. 4, identified by Compositions 74, and 77-82, and in Series X(b), FIG. 5, identified by Compositions 83, and 86-91. It will be appreciated that $R_4$ may be positioned at one or more locations of the phenyl ring as set forth in Formula 32.

The present invention provides a composition of the Formula 3:

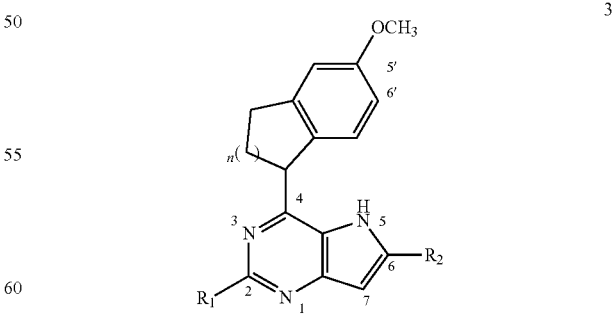

when n = 1
when n = 2 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein n is 1 or 2; and optionally comprising stereochemical conformations thereof; and optionally comprising a pharmaceutically acceptable salt thereof. Preferred embodiments of the compositions embodied by Formula 3 are set forth in Series XI, FIG. 5, identified by Composition 92 (where n=1) and Composition 93 (where n=2).

The present invention provides a composition of Formula 4:

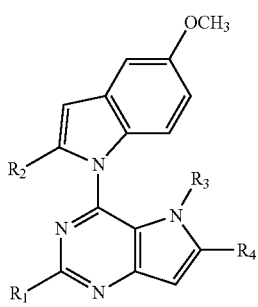

4 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and wherein $R_4$ is selected from the group consisting of H and a straight chain or branched chain alkyl group having from 1 to 10 carbon atoms; and optionally comprising stereochemical conformations thereof; and optionally comprising a pharmaceutically acceptable salt thereof. Preferred embodiments of the compositions embodied by Formula 4 are set forth in Series XII, FIG. 6, identified by Compositions 94-97.

The present invention provides a composition of the Formula 10:

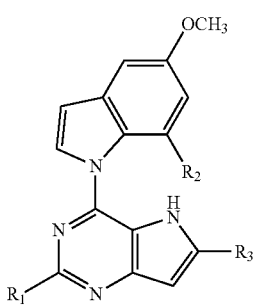

10 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and optionally comprising stereochemical conformations thereof; and optionally comprising a pharmaceutically acceptable salt thereof. A preferred embodiment of the compositions embodied by Formula 10 is set forth in Series XVI(b), FIG. 9, identified by Composition 112.

The present invention provides a composition of the Formula 11:

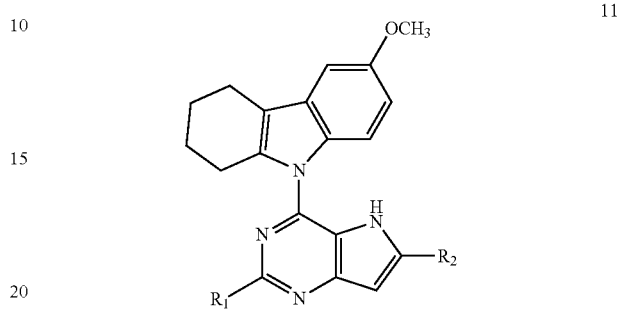

11 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and optionally comprising stereochemical conformations thereof; and optionally comprising a pharmaceutically acceptable thereof. A preferred embodiment of the compositions embodied by Formula 11 is set forth in Series XVI(c), FIG. 9, identified by Composition 113.

The present invention provides a composition of the Formula 12:

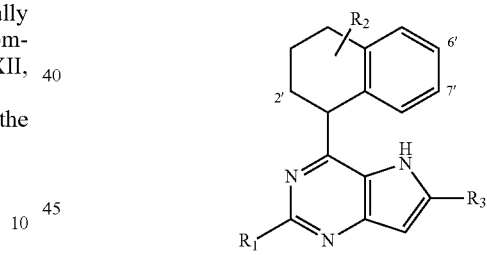

comprising wherein $R_1$ is selected from the group consisting of H, $NH_2$, and a straight chain or branched chain alkyl group having from 1 to 10 carbon atoms; and wherein $R_2$ is selected from the group consisting of (a) 2'-$CH_3$, 6'-$OCH_3$, (b) 7'-$OCH_3$, 6'-$OCH_3$, (c) 7'-OH, 6'-$OCH_3$, (d) 2'-$CH_3$, 6'-OH, and (e) 6'-$OCF_3$; and wherein $R_3$ is selected from the group consisting of H and a straight chain or branched chain alkyl group having from 1 to 10 carbon atoms; and optionally comprising stereochemical conformations thereof; and optionally comprising a pharmaceutically acceptable salt thereof. Preferred embodiments of the compositions embodied by Formula 12 are set forth in Series XVII, FIG. 10, identified by Compositions 114-118. It will be appreciated that $R_2$ may be positioned at one of the 2', 6', and 7' positions of one of the two upper rings, and that R2 may be positioned at one or more (multiple) locations of one or both of the two upper rings at positions 2', 6', and 7', and combinations thereof.

The present invention provides a composition of the Formula 33:

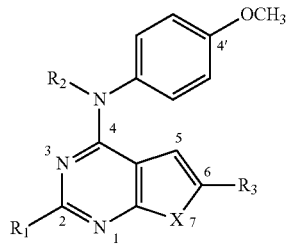

33 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and wherein X is S; and optionally comprising stereochemical conformations thereof; and optionally comprising a pharmaceutically acceptable salt thereof. A preferred embodiment of the compositions embodied by Formula 33 is set forth in Series XVIII, FIG. 10, identified by Composition 121.

The present invention providers a composition of Formula 35:

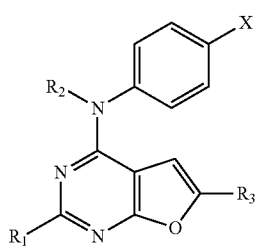

35 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and wherein X is $SCH_3$; and optionally comprising stereochemical conformations thereof; and optionally comprising a pharmaceutically acceptable thereof. A preferred embodiment of the compositions embodied by Formula 35 is set forth in Series XX, FIG. 11, identified by Composition 125.

The present invention provides for a composition of Formula 21:

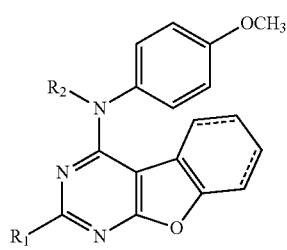

21 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and optionally comprising stereochemical conformations thereof; and optionally comprising a pharmaceutically acceptable thereof. A preferred embodiment of the compositions embodied by Formula 21 is set forth in Series XXII, FIG. 11, identified by Composition 138.

The present invention provides a composition of the Formula 13:

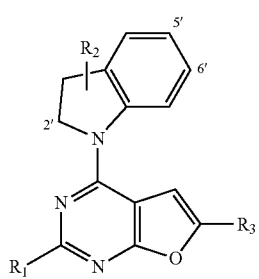

13 comprising wherein $R_1$ is selected from the group consisting of H, $NH_2$, and a straight chain or branched chain alkyl group having from 1 to 10 carbon atoms; and wherein $R_2$ is selected from the group consisting of (a) 2'-$CH_3$, 5'-$OCH_3$, (b) 6'-$OCH_3$, 5'-$OCH_3$, and (c) 5'-$OCH_2CH_3$; and wherein R3 is selected from the group consisting of H and a straight chain or branched chain alkyl group having from 1 to 10 carbon atoms; and optionally comprising stereochemical conformations thereof; and optionally comprising a pharmaceutically acceptable salt thereof. Preferred embodiments of the compositions embodied by Formula 13 are set forth in Series XXIII(a), FIG. 12, identified by Compositions 139-141. It will be appreciated that $R_2$ may be positioned at one of the 2', 5', and 6' positions of one of the two upper rings, and that R2 may be positioned at one or more (multiple) locations of one or both of the two upper rings at positions 2', 5', and 6', and combinations thereof.

The present invention provides a composition of the Formula 14:

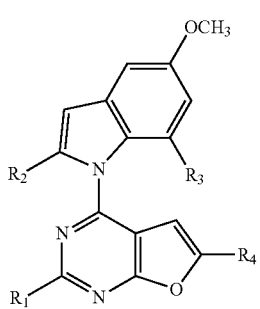

14 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and wherein $R_4$ is selected from the group consisting of H and a straight chain or branched chain alkyl group having from 1 to 10 carbon atoms; and optionally comprising stereochemical conformations thereof; and optionally comprising a pharmaceutically acceptable salt thereof. Preferred embodiments of the compositions embodied by Formula 14 are set forth in Series XXIII(b), FIG. 12, identified by Compositions 142-144.

The present invention provides a composition of the Formula 15:

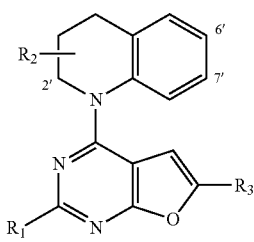

15 comprising wherein $R_1$ is selected from the group consisting of H, $NH_2$, and a straight chain or branched chain alkyl group having from 1 to 10 carbon atoms; and wherein $R_2$ is selected from the group consisting of (a) 2'-$CH_3$, 6'-$OCH_3$, (b) 7'-$OCH_3$, 6'-$OCH_3$, (c) 7'-OH, 6'-$OCH_3$, (d) 2'-$CH_3$, 6'-OH, and (e) 6'-$OCF_3$; and wherein $R_3$ is selected from the group consisting of H and a straight chain or branched chain alkyl group having from 1 to 10 carbon atoms; and optionally comprising stereochemical conformations thereof; and optionally comprising a pharmaceutically acceptable salt thereof. Preferred embodiments of the compositions embodied by Formula 15 are set forth in Series XXIV, FIG. 13, identified by Compositions 146-150. It will be appreciated that $R_2$ may be positioned at one of the 2', 6', and 7' positions of one of the two upper rings, and that R2 may be positioned at one or more (multiple) locations of one or both of the two upper rings at positions 2', 6', and 7', and combinations thereof.

The present invention provides a composition of the Formula 16:

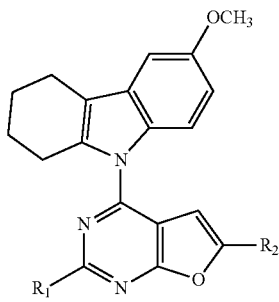

16 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and optionally comprising stereochemical conformations thereof; and optionally comprising a pharmaceutically acceptable salt thereof. A preferred embodiment of the compositions embodied by Formula 16 is set forth in Series XXIII(c), FIG. 12, identified by Composition 145.

Water soluble salts, such as for example HCL salts (or other acids), of the compositions of Formulae 1-5, 7-21, 24, 32, 33 and 35 of the present invention (as set forth in FIGS. 1-13) are also provided herein.

A method of treating a patient having cancer is disclosed herein comprising administering to a patient an effective amount of a composition selected from the group consisting of compositions of Formulae 1-5, 7-21, 24, 32, 33, and 35, and salts thereof, for treating the patient. Further, a method of treating a patient with macular degeneration or arthritis is disclosed herein comprising administering to a patient an effective amount of a composition of the present invention as identified by Formulae 1-5, 7-21, 24, 32, and 35, and salts thereof, for treating the patient having macular degeneration or arthritis. Further, a method of treating a patient having cancer comprising inhibiting VEGFR2 receptors and tubulin assembly by administering a therapeutically effective amount of at least one composition of Formulae 1-5, 7-21, 24, 32, 33, and 35, and salts thereof, to the patient.

BRIEF DESCRIPTION OF THE DRAWINGS

A full description of the invention may be gained from the following description of the preferred embodiments of the invention when read in conjunction with the accompanying drawings in which:

FIGS. 1-13 show the chemical structures of the preferred compositions of the present invention. FIG. 7 shows the chemical structure of a more preferred embodiment of the present invention, namely, the chemical structure of chemical Composition No. 104 which is also identified herein as sample identification number RP/AG/159-249 (or "RP 249"). FIG. 8 shows the chemical structure of another preferred embodiment of the present invention, namely, the chemical structure of chemical Composition No. 106. The HCl salt of chemical Composition No. 106 is identified herein as sample identification number RP/AG/159-248 (or "RP 248"). As used herein, the term "benzyl" means —$CH_2$-phenyl. FIG. 4, Series Xa, Composition No. 80 shows that the R group 2',3'-$(CH)_4$ is attached to the lower right ring to form a composition having a 1-naphthyl moiety, and that Composition 81 shows that the R group 3',4'-$(CH)_4$ is attached to the lower right ring to form a composition having a 2-naphthyl moiety. FIG. 5, Series Xb, Composition No. 89 shows that the R group 2',3'-$(CH)_4$ is attached to the lower right ring to form a composition having a 1-naphthyl moiety, and that Composition 90 shows that the R group 3',4'-$(CH)_4$ is attached to the lower right ring to form a composition having a 2-naphthyl moiety. It will be understood by those persons skilled in the art that many of the other compositions of the present invention recite a R group that is —$(CH)_4$ and that is attached to a ring for forming a composition having a naphthyl moiety. The compositions shown in FIG. 1 through FIG. 13 have VEGFR2 inhibition, antitubulin activity, and cytotoxic activity against tumor cells.

FIG. 14 shows National Cancer Institute data on 60 tumor cell lines for Composition 104 (RP 249).

FIG. 15 shows RP 249 as inhibiting tubulin assembly having an $IC_{50}$ of 1.2 μM.

FIG. 16 shows a comparison of RP 249 against VEGFR2 (Flk-1) with known VEGFR2 inhibitors such as SU5416, Sunitinib.

FIG. 18 shows the synthesis scheme for Composition 104 (RP249) of the present invention.

FIG. 19 shows the kinase inhibition and A431 cytotoxicity of Composition 106 as the HCl salt formulation as compared to commercially available compositions cisplatin, sunitinib, and erlotinib.

FIG. 20 shows the National Cancer Institute data on 60 tumor cell lines for Composition 106 as the HCl (hydrochloride) salt formulation.

FIGS. 22A, 22B, and 22 C show the National Cancer Institute Developmental Therapeutics program Dose Response Curves for Composition 106 as the HCl salt formulation concerning 57 tumor cell lines.

FIGS. 24-30 provide synthesis schematics of the compositions of this invention.

DESCRIPTION OF THE PREFERRED EMBODIMENTS

Figure 13:
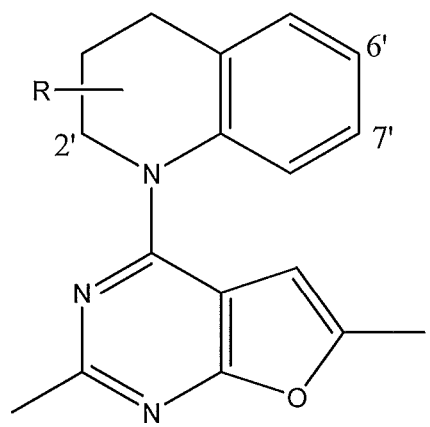

As used herein, the term "patient" means members of the animal kingdom, including but not limited to, human beings.

As used herein, the term "an effective amount" or "therapeutically effective amount" refers to that amount of any of the present compositions or salts thereof required to bring about a desired effect in a patient. The desired effect will vary depending on the illness being treated. For example, the desired effect may be reducing the tumor size, destroying cancerous cells, and/or preventing metastasis, any one of which may be the desired therapeutic response. On its most basic level, a therapeutically effective amount is that amount of a substance needed to inhibit mitosis of a cancerous cell.

The remarkable clinical success and the hundreds of ongoing clinical trials of antiangiogenic agents (AAs), particularly VEGFR2 inhibitors, and in combination with antitubulins, attests to the clinical importance of this combination in cancer chemotherapy. Combination chemotherapy with the use of two separate agents is not a new idea, however, the present invention provides compositions that have the attributes of VEGFR2 inhibition along with antitubulin activity in a single molecule and thus are novel over the background art. In addition, the compositions of the present invention are highly water soluble and are not subject to Pgp efflux, and thus the present compositions overcome some of the important drawbacks of taxanes and the *Vinca* alkaloids. In addition, the present compositions inhibit almost all the tumor cells in the NCI 60 tumor panel with $GI_{50}$ values of $10^{-7}$-$10^{-8}$ M, including those that were taxol resistant and demonstrated potent in vivo antitumor activity and antiangiogenic activity against triple negative breast cancer mouse models better than paclitaxel alone or sunitinib alone, without toxicity.

The present invention meets the above described need by providing bicyclic and tricyclic pyrimidine compositions that have dual (combined) activity, namely, vascular endothelial growth factor receptor inhibitory activity and antitubulin activity.

The present invention provides a composition of the Formula 5:

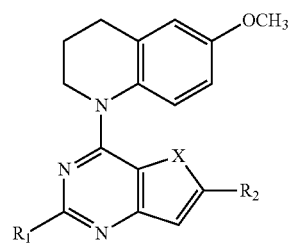

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein X is selected from the group consisting of NH, $NCH_3$, O, and S; and optionally comprising stereochemical conformations thereof; and optionally comprising a pharmaceutically acceptable salt thereof. Preferred embodiments of the compositions embodied by Formula 5 are set forth in Series XIII, FIG. 6, identified by Compositions 98-100, and Series XIV, FIG. 7, identified by Compositions 101-103, and Series XVa, FIG. 7, Composition 104. Composition 104 is also referred to herein as "RP249" and/or "RP/AG/159-249".

The present invention provides a composition of Formula 7:

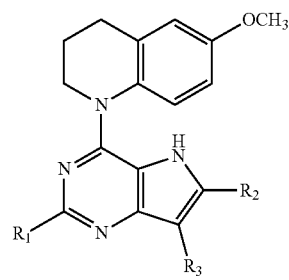

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H, a phenyl group, a substituted phenyl group, a benzyl group, a substituted benzyl group, and a straight chain or branched chain alkyl group having from 1 to 10 carbon atoms, and wherein the alkyl group is optionally substituted with one or more of a phenyl group or a substituted phenyl group, or combinations thereof; and wherein each of the substituents of any of the substituted groups is the same or different and are selected from the group consisting of an electron withdrawing group and an electron donating group, and combinations thereof; and optionally comprising stereochemical conformations thereof; and optionally comprising a pharmaceutically acceptable salt thereof. Preferred embodiments of the compositions embodied by Formula 7 are set forth in Series XIV, Compositions 101-103, FIG. 7, and Series XVa, Compositions 104-105, FIG. 7.

As used herein, the term "electron withdrawing group" or "EWG" is a functional group that draws electrons away from a reaction center. For example, but not limited to, an electron withdrawing group is a halogen (for example, but not limited to Cl and F), a nitrile (CN), a carbonyl (CO), a trihalide (for example but not limited to, —CF₃, and —CCl₃), —OCF₃, and a nitro group (NO₂). As used herein, the term "electron donating group" or EDG" is a functional group that releases electrons into a reaction center. For example, but not limited to, an electron donating group is an alkyl group having from 1 to 10 carbon atoms (for example, but not limited to CH₃, CH₂CH₃, and CH₂CH₂CH₃), alcohol groups, alkoxy groups (for example, OCH₃), and amino groups.

The polar effect or electronic effect in chemistry is the effect exerted by a substituent on modifying electrostatic forces operating on a nearby reaction center. The total substituent effect is the combination of the polar effect and the combined steric effects. In electrophilic aromatic substitution and nucleophilic aromatic substitution, substituents are divided into activating groups and deactivating groups where the direction of activation or deactivation is also taken into account. A functional group is an activating group (or electron donating group), for example, if a benzene molecule to which it is attached more readily participates in electrophilic substitution reactions. A deactivating group (or electron withdrawing group), for example, is a functional group attached to a benzene molecule that removes electron density from the benzene ring, making electrophilic aromatic substitution reactions slower.

The present invention provides a composition of the Formula 8:

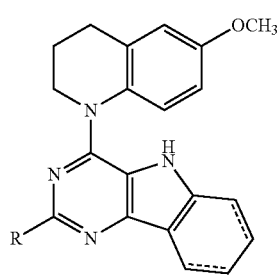

8 comprising wherein R is selected from the group consisting of H, NH₂, and a straight chain or branched chain alkyl group having from 1 to 10 carbon atoms; and optionally comprising stereochemical conformations thereof; and optionally comprising a pharmaceutically acceptable salt thereof. Preferred embodiments of the composition embodied by Formula 8 is set forth in Series XVb, FIG. 8, identified by Composition 106. The hydrochloride salt formulation of Composition 106 is also referred to herein as "RP248" and/or "RP/AG/159-248". It will be appreciated that the lower far right ring of the chemical structure set forth in Formula 8 (and in Formula 21 herein) may be completely unsaturated, partially unsaturated, or partially saturated as indicated by the broken double lines in the ring.

The compositions of the present invention as described hereinabove and herein below remarkably possess all the attributes described above and also inhibit tubulin assembly, bind to the colchicine site on tubulin (as distinct from taxane and Vincas), inhibit VEGFR2 at levels similar to sunitinib and semaxinib, and afford antiangiogenic activity in the CAM assay. It will be appreciated by those persons skilled in the art that the present compositions combine the cytostatic activity of VEGFR2 inhibitors along with the cytotoxic activity of antitubulin agents in a single agent and thus have all the advantages of combination chemotherapy when two separate agents, VEGFR2 inhibitors and antitubulins, delay or prevent tumor resistance. A further advantage of the present compositions is that they do not suffer from the pharmacokinetic disadvantages of drug-drug interactions, overlapping toxicities, lack of patient compliance, and the high cost associated with use of two separate drugs in combination. Most importantly, the single agent compositions of the present invention provide the antitubulin cytotoxic effect in the same molecule as the antiangiogenic VEGFR2 inhibitory effect such that the cytotoxic effect is manifested at the same time in the same place where the VEGFR2 antiangiogenic effect is operable. Since the tumor is usually heterogeneous, a separately dosed cytotoxic antitubulin (as discussed in the background art section) may miss the transient windows of tumor vasculature normalization via VEGFR2 inhibition (unless the antitubulin is administered metronomically) and thus precludes the intent of combination therapy. Antitubulin activity along with VEGFR2 activity in single agents manifest tumor cytotoxicity at the time dictated by the antiangiogenic effects. The single agent compositions of the present invention are on the spot for uptake into the tumor for the cytotoxic action as soon as or even during vasculature normalization due to the angiogenic effects. Such on the spot agents are much more efficient in getting into the tumor and do not need to be as potent as conventional separately dosed cytotoxic agents, thus reducing one of the major obstacles to combination chemotherapy—dose related toxicity. The present compositions having antimitotic and antiangiogenic activities are in keeping with the two mechanisms, metronomic dosing, and transient vascular normalization, that explain the clinical success of VEGFR2 inhibitors and antitubulin agents in combination chemotherapy. Thus, the compositions of the present invention afford cancer treatment options alone and in combination and for the vast majority of patients that become resistant to other antitumor agents and antitubulins.

In additional embodiments of the present invention, additional compositions having the structures set forth below are provided. These additional compositions of the present invention set forth below and in FIGS. 1-13, for convenience of this application, are placed in the following optimized structural Series I, II, III, IV, VIII, X through XVIII, XX, and XXII through XXIV. These additional compositions of the present invention each have VEGFR2 inhibition, antitubulin activity and cytotoxic activity against tumor cells. The applicant realizes that the structural requirements for each of the compositions of the different Series set forth herein for VEGFR2, tubulin and tumor cell inhibition may be different (i.e. structural features for compositions of Series I, for example, for VEGFR2 inhibition, may be different than that for tubulin inhibition and different for tumor cell inhibition). Thus, "optimization" of the structures as set forth in the various Series (see FIGS. 1-13) of compositions of this invention will provide chemical structural features that afford the best balance of potency against all three primary evaluations (VEGFR2, tubulin and tumor cell inhibition). It is also important to note that the HCl or other acid salts of all of the structures of the chemical compositions set forth in this Application (except perhaps for compositions of Series XI) can be easily synthesized by those persons skilled in the art.

For each of the compositions in the above mentioned Series (except Series XI) it has been determined that for antitubulin activity, the 4-position needs to have a N+CH₃-

4-OMe-aniline or some variation that includes all three aspects (NCH₃, 4-OMe, C₆H₄), thus all of the compositions of the Series of the present invention contain this structural requirement.

Series I-II compositions address the bulk and conformational restriction of the 4-anilino moiety.

Series III compositions extends the chain length between the 4-OMePh and the 4-position to determine optimum distance.

Series IV compositions show the importance to activity of the pyrrole NH and its intra- and intermolecular H-bonding ability.

Series VIII compositions show the optimum distance and bond angle or the benzylic atom of the pyrrolo[3,2-d]pyrimidine and the 7-benzyl group. In addition, the $R_1$, $R_2$, and $R_3$ restrict conformational rotation of the 7-benzyl group to determine optimal conformation(s) for activity of the 7-benzyl moiety relative to the pyrrolo[3,2-d]pyrimidine. In the N5-CH₃ analogs in Series VIII, the nature of the N5-H and its ability to H-bond and restrict conformational rotation and the effect on biological activity are set forth.

Series XIII, XIV, XV, XVII, and XXIV compositions all address the size and conformation of the 4-(6'-OMe) tetrahydroquinoline.

Figure 17:
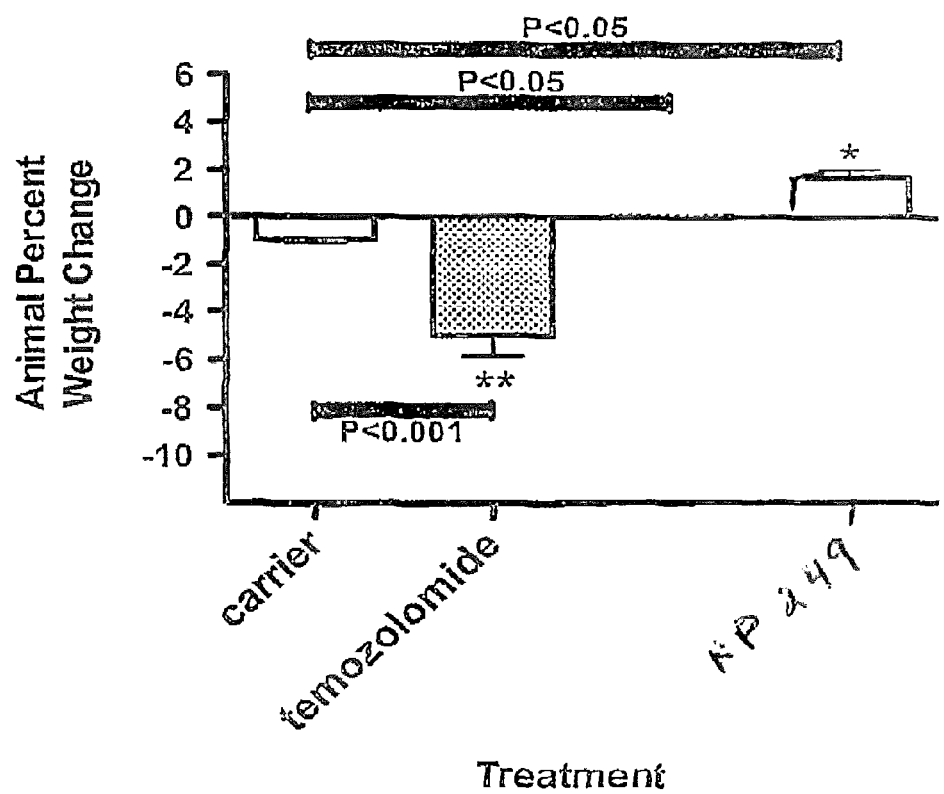
FIG. 17 shows U251 flank animal weight change (animal has flank xenograft implant) with treatment with Composition 104 (RP249) of the present invention.
Figure 21:
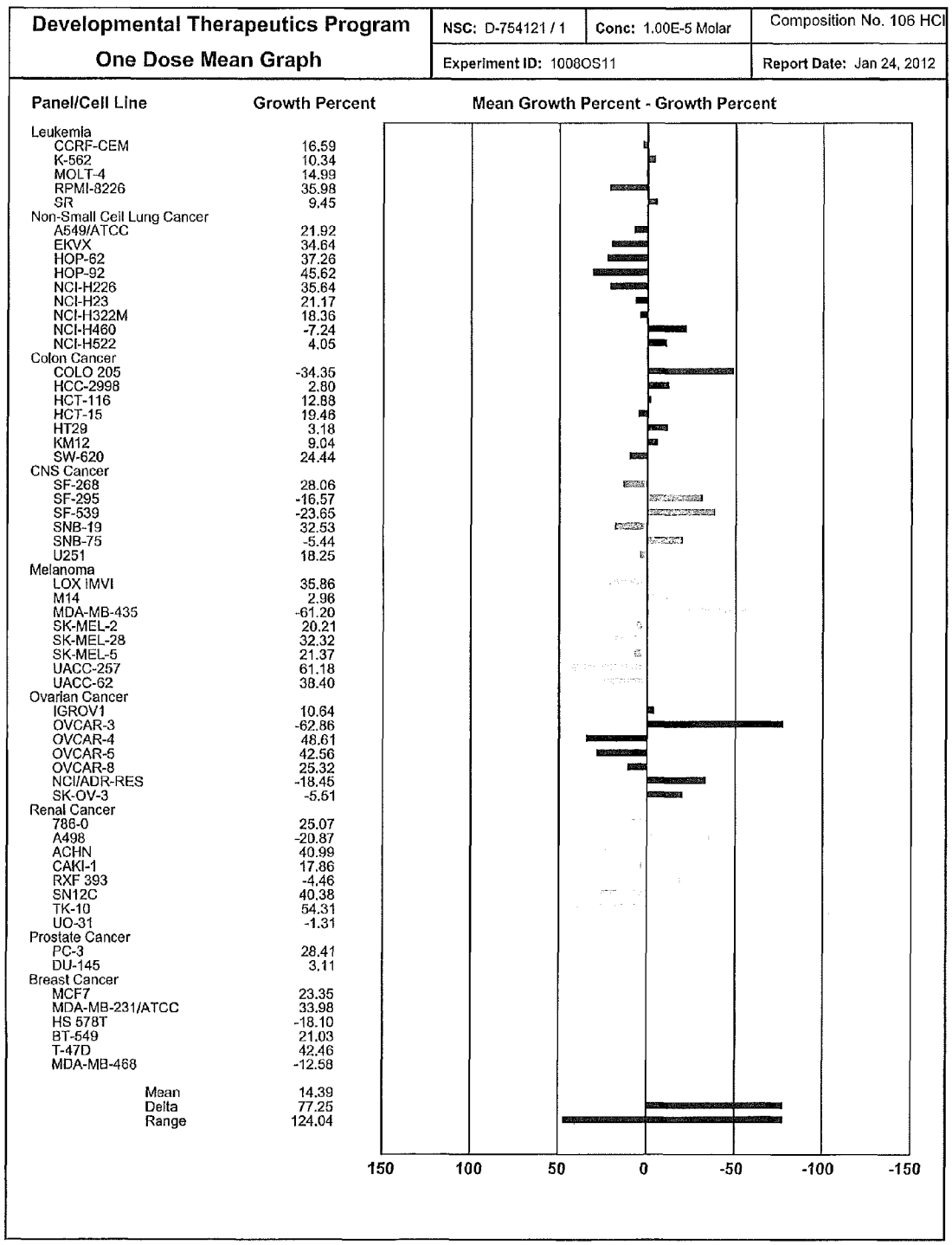
FIG. 21 shows the National Cancer Institute Developmental Therapeutics Program One Dose Mean Graph data for Composition 106 as the HCl salt formulation for 58 tumor cell lines.
Figure 22A:
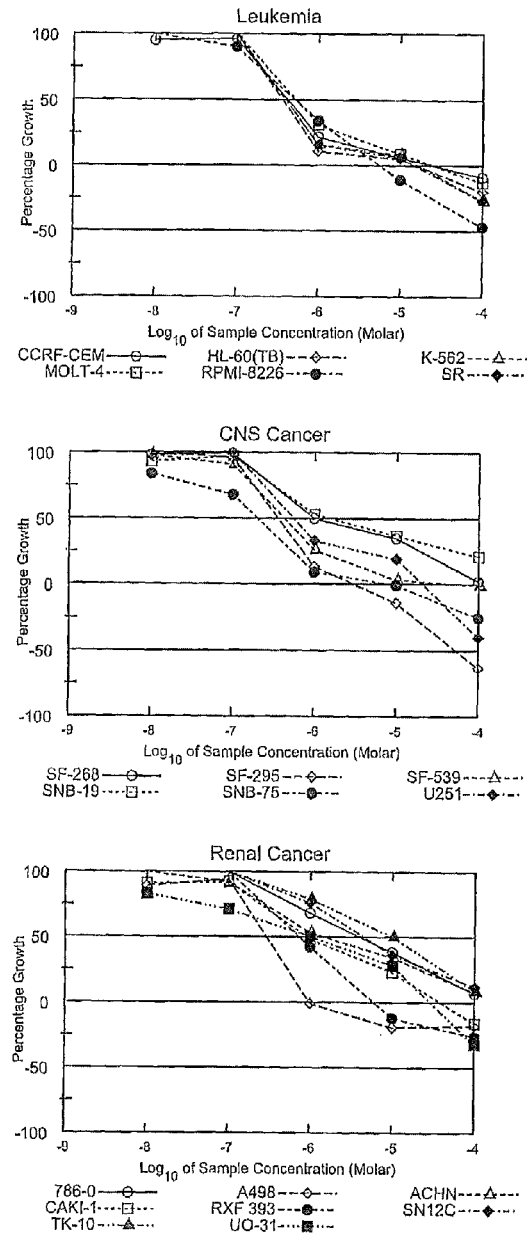
Figure 22B:
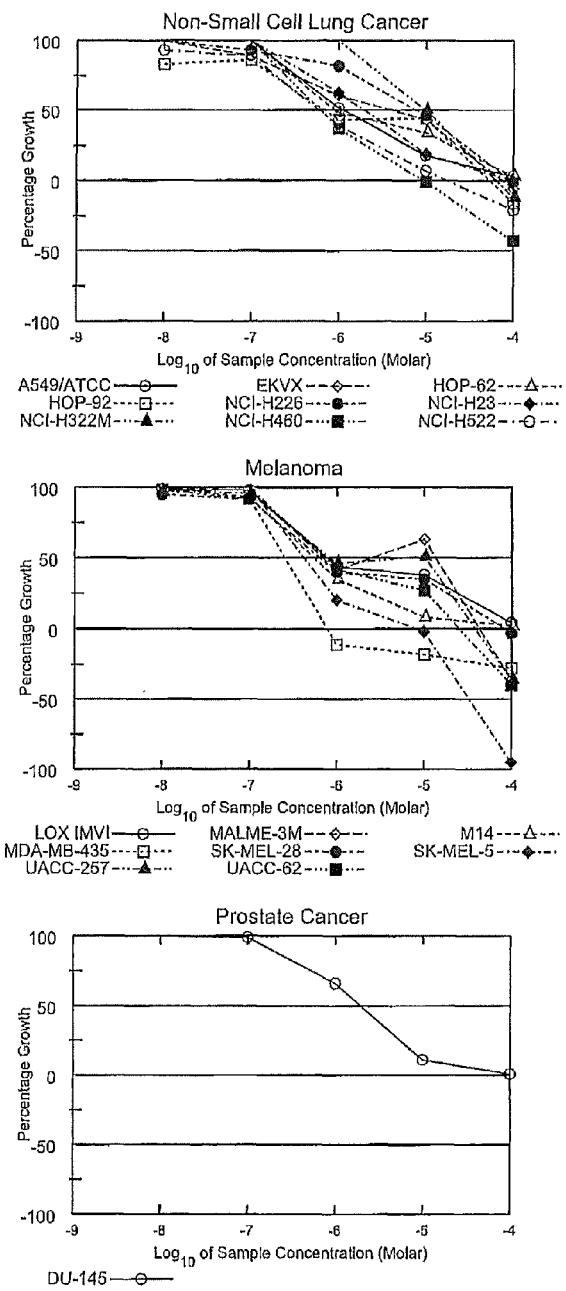
Figure 23:
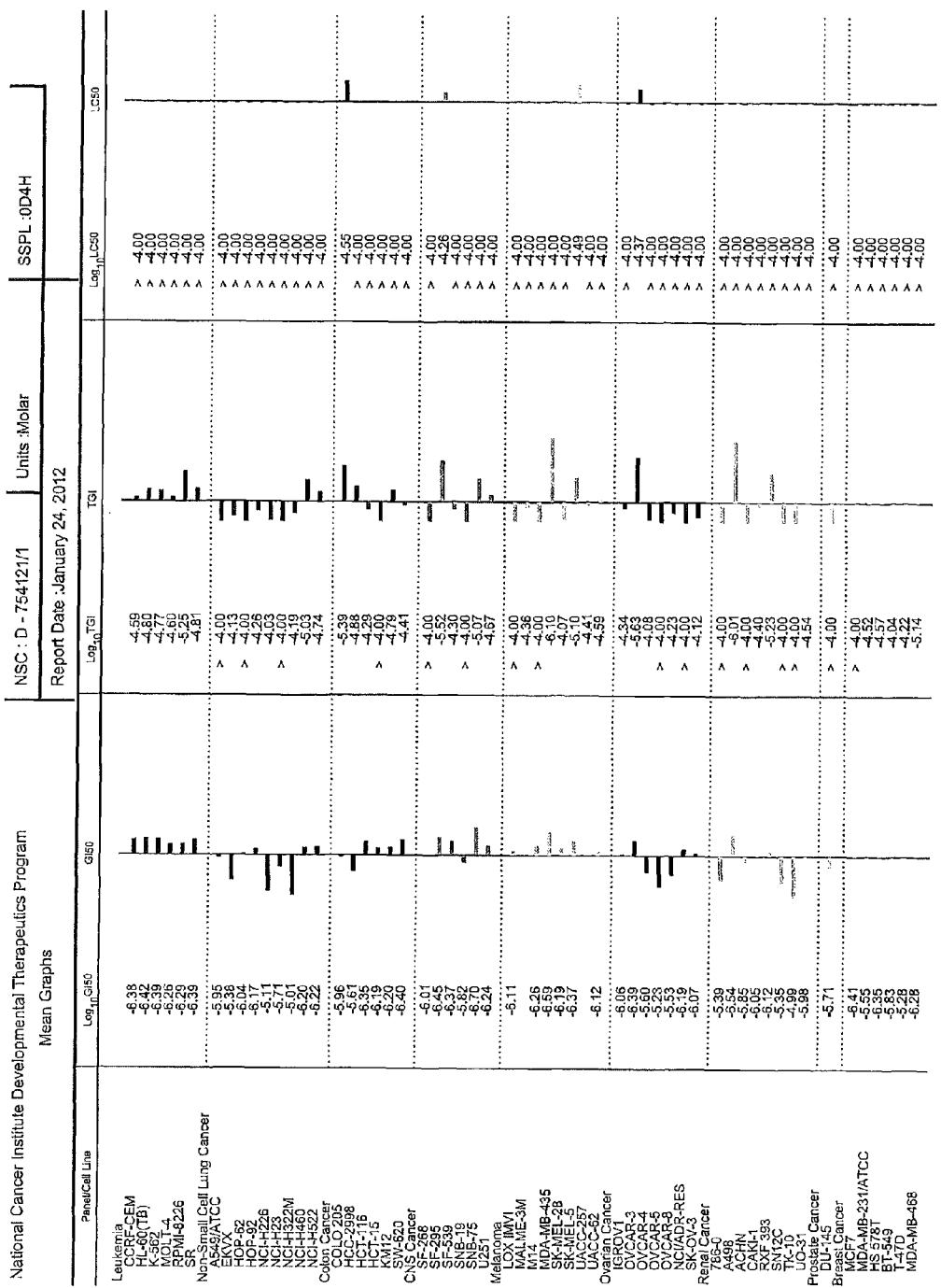
FIG. 23 shows the National cancer Institute Developmental Therapeutics Program Mean Graph data for Composition 106 as the HCl salt formulation against 57 tumor cell lines.

The compositions of Series XVI and XVII show conformational restriction at the 4-position. The 4-position substitution of Composition 104 is a tetrahydroquinoline. FIG. 14 shows National Cancer Institute data on 60 tumor cell lines for Composition 104, a dual acting antitubulin/VEGFR2 inhibitor of the present invention, also identified herein as RP 249 and RP/AG/159-249. FIG. 15 shows RP 249 as inhibiting tubulin assembly having an $IC_{50}$ of 1.2 µM. FIG. 16 shows a comparison of Composition 104 of the present invention, namely RP 249, against VEGFR2 (Flk-1) with known VEGFR2 inhibitors such as SU5416, Sunitinib. RP 249 is 30.6 µM against VEGFR2 comparable to the current standards at 12.9 and 18.9 µM. FIG. 17 shows U251 flank animal weight change with treatment with Composition 104 of the present invention.

The present invention provides a composition of the Formula 9:

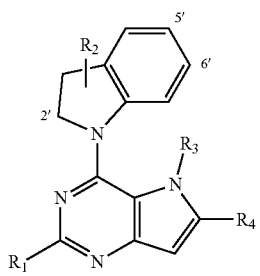

comprising wherein $R_1$ is selected from the group consisting of H, NH₂, and a straight chain or branched chain alkyl group having from 1 to 10 carbon atoms; and wherein $R_2$ is selected from the group consisting of (a) 2'-CH₃, 5'-OCH₃, (b) 6'-OCH₃, 5'-OCH₃, (c) 5'-OCH₂CH₃, and (d) 5'-OCH₃; and wherein $R_3$ is selected from the group consisting of H and a straight chain or branched chain alkyl group having from 1 to 10 carbon atoms; and wherein $R_4$ is selected from the group consisting of H and a straight chain or branched chain alkyl group having from 1 to 10 carbon atoms; and optionally comprising stereochemical conformations thereof; and optionally comprising a pharmaceutically acceptable salt thereof. Preferred embodiments of the compositions embodied by Formula 9 are set forth in Series XVIa, FIG. 8, identified by Compositions 107-111. It will be will be understood that $R_2$ may be positioned at one of the 2', 5', and 6' positions of one of the two upper rings, and that $R_2$ may be positioned at one or more (multiple) locations of one or both of the two upper rings at positions 2', 6', and 7', and combinations thereof.

The present invention provides a composition of Formula 17:

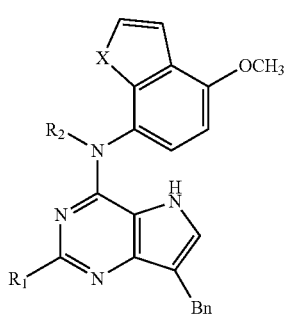

comprising wherein $R_1$ is selected from the group consisting of H, NH₂, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein X is selected from the group consisting of (a) CH=CH, (b) NH, (c) NCH₃, (d) O, and (e) S; wherein Bn is selected from the group consisting of H, a phenyl group, a substituted phenyl group, a benzyl group, a substituted benzyl group, and a straight chain or branched chain alkyl group having from 1 to 10 carbon atoms, and wherein said alkyl group is optionally substituted with one or more of a phenyl group or a substituted phenyl group, or combinations thereof; and wherein each of said substituents of any said substituted group is the same or different and are selected from the group consisting of an electron withdrawing group and an electron donating group, and combinations thereof; and optionally comprising stereochemical conformations thereof; and optionally comprising a pharmaceutically acceptable salt thereof. Preferred embodiments of the compositions embodied by Formula 17 are set forth in Series I, FIG. 1, identified by Compositions 4-8.

The present invention provides a composition of Formula 1:

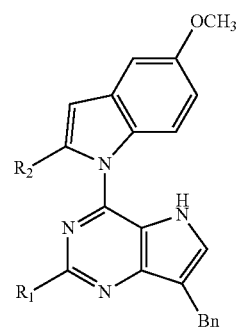

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; wherein Bn is selected from the group consisting of H, a phenyl group, a substituted phenyl group, a benzyl group, a substituted benzyl group, and a straight chain or branched chain alkyl group having from 1 to 10 carbon atoms, and wherein said alkyl group is optionally substituted with one or more of a phenyl group or a substituted phenyl group, or combinations thereof; and wherein each of said substituents of any said substituted group is the same or different and are selected from the group consisting of an electron withdrawing group and an electron donating group, and combinations thereof; and optionally comprising stereochemical conformations thereof; and optionally comprising a pharmaceutically acceptable salt thereof. Preferred embodiments of the compositions embodied by Formula 1 are set forth in Series IIa, FIG. 1, identified by Compositions 15 and 16.

The present invention provides a composition of Formula 2:

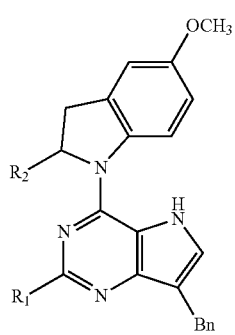

2 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; wherein Bn is selected from the group consisting of H, a phenyl group, a substituted phenyl group, a benzyl group, a substituted benzyl group, and a straight chain or branched chain alkyl group having from 1 to 10 carbon atoms, and wherein said alkyl group is optionally substituted with one or more of a phenyl group or a substituted phenyl group, or combinations thereof; and wherein each of said substituents of any said substituted group is the same or different and are selected from the group consisting of an electron withdrawing group and an electron donating group, and combinations thereof; and optionally comprising stereochemical conformations thereof; and optionally comprising a pharmaceutically acceptable salt thereof. Preferred embodiments of the compositions embodied by Formula 2 are set forth in Series IIb, FIG. 2, identified by Compositions 17 and 18.

The present invention provides a composition of the Formula 18:

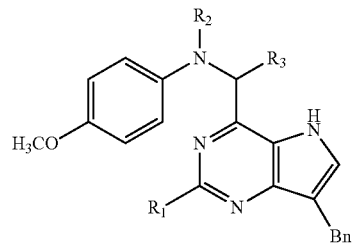

18 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and wherein Bn is selected from the group consisting of H, a phenyl group, a substituted phenyl group, a benzyl group, a substituted benzyl group, and a straight chain or branched chain alkyl group having from 1 to 10 carbon atoms, and wherein said alkyl group is optionally substituted with one or more of a phenyl group or a substituted phenyl group, or combinations thereof; and wherein each of said substituents of any said substituted group is the same or different and are selected from the group consisting of an electron withdrawing group and an electron donating group, and combinations thereof; and optionally comprising stereochemical conformations thereof; and optionally comprising a pharmaceutically acceptable salt thereof. Preferred embodiments of the compositions embodied by Formula 18 are set forth in Series III, FIG. 2, identified by Compositions 22-24.

The present invention provides a composition of Formula 24:

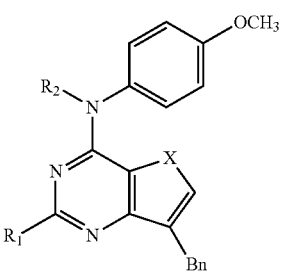

24 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein X is S; and wherein Bn is selected from the group consisting of H, a phenyl group, a substituted phenyl group, a benzyl group, a substituted benzyl group, and a straight chain or branched chain alkyl group having from 1 to 10 carbon atoms, and wherein said alkyl group is optionally substituted with one or more of a phenyl group or a substituted phenyl group, or combinations thereof; and wherein each of said substituents of any said substituted group is the same or different and are selected from the group consisting of an electron withdrawing group and an electron donating group, and combinations thereof; optionally comprising stereochemical conformations thereof; and optionally comprising a pharmaceutically acceptable salt thereof. A preferred embodiment of the compositions embodied by Formula 24 is set forth in Series IV, FIG. 3, identified by Composition 27.

The present invention provides a composition of the Formula 19:

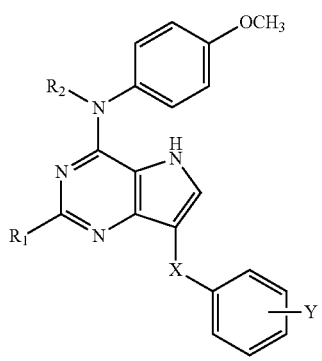

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein X is selected from the group consisting of (a) NH, (b) $NCH_3$, (c) O, and (d) S; and wherein Y is selected from the group consisting of H, $CH_3$, $(CH)_4$, Cl, and $OCH_3$, wherein Y may be attached to the ring at one or more positions and may be the same or different; and optionally comprising stereochemical conformations thereof; and optionally comprising a pharmaceutically acceptable salt thereof. Preferred embodiments of the compositions embodied by Formula 19 are set forth in Series VIIIa, FIG. 3, identified by Compositions 50-57.

The present invention provides a composition of the Formula 20:

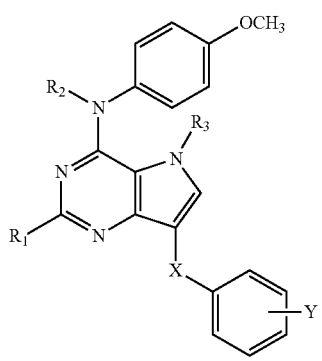

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and wherein X is selected from the group consisting of (a) NH, (b) $NCH_3$, (d) O, and (e) S; and wherein Y is selected from the group consisting of H, $CH_3$, $(CH)_4$, Cl, and $OCH_3$, and wherein Y may be attached to the ring at one or more positions and may be the same or different; and optionally comprising stereochemical conformations thereof; and optionally comprising a pharmaceutically acceptable salt thereof. Preferred embodiments of the compositions embodied by Formula 20 are set forth in Series VIIIb, FIG. 4, identified by Compositions 58-65.

The present invention provides a composition of Formula 32:

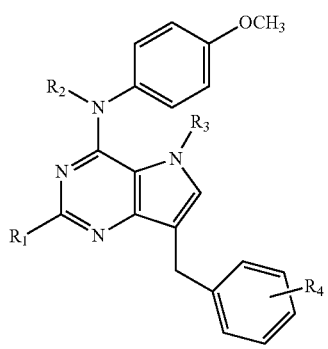

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein R3 is selected from the group consisting of H and a straight or branched chain alkyl group having from 1 to 10 carbon atoms, and wherein $R_4$ is selected from the group consisting of (a) 2',6'-di$CH_3$, (b) 2',5'-di$OCH_3$, (c) 2',4'-diCl, (d) 3',4'-diCl, (e) 2',3'-$(CH)_4$, (f) 3',4'-$(CH)_4$, and (g) 3',4',5'-tri$OCH_3$; and optionally comprising stereochemical conformations thereof; and optionally comprising a pharmaceutically acceptable salt thereof. Preferred embodiments of the compositions embodied by Formula 32 are set forth in Series X(a), FIG. 4, identified by Compositions 74, and 77-82, and in Series X(b), FIG. 5, identified by Compositions 83, and 86-91. It will be appreciated from the structure of Formula 32 that $R_4$ may be attached to the phenyl ring at one or more positions (i.e. at multiple positions of the phenyl ring).

The present invention provides a composition of the Formula 3:

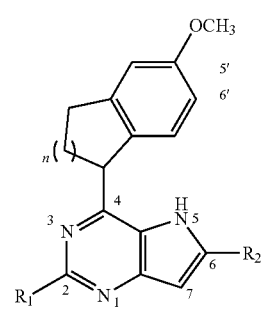

when n = 1
when n = 2 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein n is 1 or 2; and optionally comprising stereochemical conformations thereof; and optionally comprising a pharmaceutically acceptable salt thereof. Preferred embodiments of the compositions embodied by Formula 3 are set forth in Series XI, FIG. 5, identified by Composition 92 (where n=1) and Composition 93 (where n=2).

The present invention provides a composition of Formula 4:

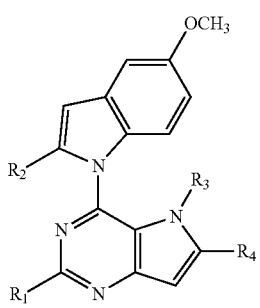

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and wherein $R_4$ is selected from the group consisting of H and a straight chain or branched chain alkyl group having from 1 to 10 carbon atoms; and optionally comprising stereochemical conformations thereof; and optionally comprising a pharmaceutically acceptable salt thereof. Preferred embodiments of the compositions embodied by Formula 4 are set forth in Series XII, FIG. 6, identified by Compositions 94-97.

The present invention provides a composition of the Formula 10:

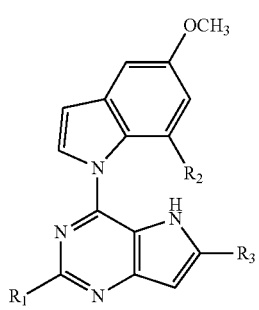

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and optionally comprising stereochemical conformations thereof; and optionally comprising a pharmaceutically acceptable salt thereof. A preferred embodiment of the compositions embodied by Formula 10 is set forth in Series XVI(b), FIG. 9, identified by Composition 112.

The present invention provides a composition of the Formula 11:

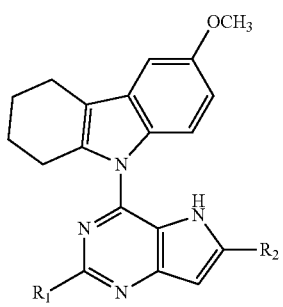

comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and optionally comprising stereochemical conformations thereof; and optionally comprising a pharmaceutically acceptable thereof. A preferred embodiment of the compositions embodied by Formula 11 is set forth in Series XVI(c), FIG. 9, identified by Composition 113.

The present invention provides a composition of the Formula 12:

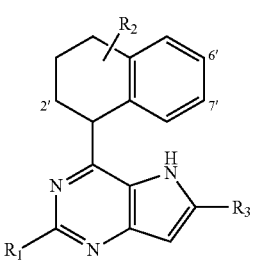

comprising wherein $R_1$ is selected from the group consisting of H, $NH_2$, and a straight chain or branched chain alkyl group having from 1 to 10 carbon atoms; and wherein $R_2$ is selected from the group consisting of (a) 2'-$CH_3$, 6'-$OCH_3$, (b) 7'-$OCH_3$, 6'-$OCH_3$, (c) 7'-OH, 6'-$OCH_3$, (d) 2'-$CH_3$, 6'-OH, and (e) 6'-$OCF_3$; and wherein $R_3$ is selected from the group consisting of H and a straight chain or branched chain alkyl group having from 1 to 10 carbon atoms; and optionally comprising stereochemical conformations thereof; and optionally comprising a pharmaceutically acceptable salt thereof. Preferred embodiments of the compositions embodied by Formula 12 are set forth in Series XVII, FIG. 10, identified by Compositions 114-118. It will be appreciated that $R_2$ may be positioned at one of the 2', 6', and 7' positions of one of the two upper rings, and that R2 may be positioned at one or more (multiple) locations of one or both of the two upper rings at positions 2', 6', and 7', and combinations thereof.

The present invention provides a composition of the Formula 33:

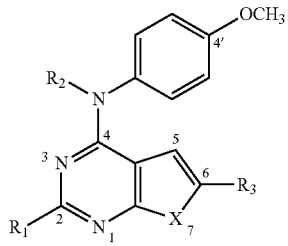

33 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and wherein X is S; and optionally comprising stereochemical conformations thereof; and optionally comprising a pharmaceutically acceptable salt thereof. A preferred embodiment of the compositions embodied by Formula 33 is set forth in Series XVIII, FIG. 10, identified by Composition 121.

The present invention providers a composition of Formula 35:

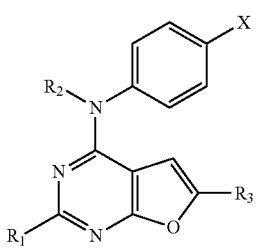

35 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and wherein X is $SCH_3$; and optionally comprising stereochemical conformations thereof; and optionally comprising a pharmaceutically acceptable thereof. A preferred embodiment of the compositions embodied by Formula 35 is set forth in Series XX, FIG. 11, identified by Composition 125.

The present invention provides for a composition of Formula 21:

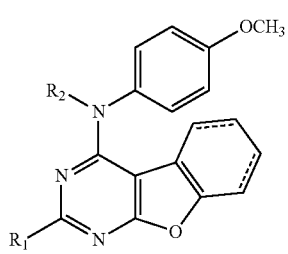

21 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and optionally comprising stereochemical conformations thereof; and optionally comprising a pharmaceutically acceptable thereof. A preferred embodiment of the compositions embodied by Formula 21 is set forth in Series XXII, FIG. 11, identified by Composition 138. It will be appreciated that the lower far right ring of the chemical structure set forth in Formula 21 may be completely unsaturated, partially unsaturated, or partially saturated as indicated by the broken double lines in the ring.

The present invention provides a composition of the Formula 13:

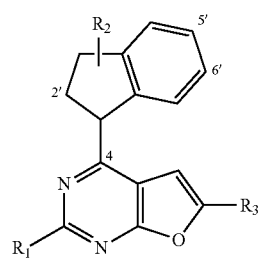

13 comprising wherein $R_1$ is selected from the group consisting of H, $NH_2$, and a straight chain or branched chain alkyl group having from 1 to 10 carbon atoms; and wherein $R_2$ is selected from the group consisting of (a) 2'-$CH_3$, 5'-$OCH_3$, (b) 6'-$OCH_3$, 5'-OCH3, and (c) 5'-$OCH_2CH_3$; and wherein R3 is selected from the group consisting of H and a straight chain or branched chain alkyl group having from 1 to 10 carbon atoms; and optionally comprising stereochemical conformations thereof; and optionally comprising a pharmaceutically acceptable salt thereof. Preferred embodiments of the compositions embodied by Formula 13 are set forth in Series XXIII(a), FIG. 12, identified by Compositions 139-141. It will be appreciated that $R_2$ may be positioned at one of the 2', 5', and 6' positions of one of the two upper rings, and that R2 may be positioned at one or more (multiple) locations of one or both of the two upper rings at positions 2', 5', and 6', and combinations thereof.

The present invention provides a composition of the Formula 14:

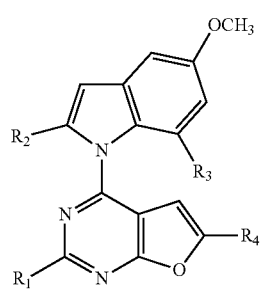

14 comprising wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein R$_3$ is selected from the group consisting of H and a straight chain or branched chain alkyl group having from 1 to 10 carbon atoms; and wherein R$_4$ is selected from the group consisting of H and a straight chain or branched chain alkyl group having from 1 to 10 carbon atoms; and optionally comprising stereochemical conformations thereof; and optionally comprising a pharmaceutically acceptable salt thereof. Preferred embodiments of the compositions embodied by Formula 14 are set forth in Series XXIII(b), FIG. 12, identified by Compositions 142-144.

The present invention provides a composition of the Formula 15:

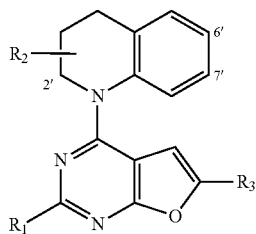

15 comprising wherein R$_1$ is selected from the group consisting of H, NH$_2$, and a straight chain or branched chain alkyl group having from 1 to 10 carbon atoms; and wherein R$_2$ is selected from the group consisting of (a) 2'-CH$_3$, 6'-OCH$_3$, (b) 7'-OCH$_3$, 6'-OCH$_3$, (c) 7'-OH, 6'-OCH$_3$, (d) 2'-CH$_3$, 6'-OH, and (e) 6'-OCF$_3$; and wherein R$_3$ is selected from the group consisting of H and a straight chain or branched chain alkyl group having from 1 to 10 carbon atoms; and optionally comprising stereochemical conformations thereof; and optionally comprising a pharmaceutically acceptable salt thereof. Preferred embodiments of the compositions embodied by Formula 15 are set forth in Series XXIV, FIG. 13, identified by Compositions 146-150. It will be appreciated that R$_2$ may be positioned at one of the 2', 6', and 7' positions of one of the two upper rings, and that R2 may be positioned at one or more (multiple) locations of one or both of the two upper rings at positions 2', 6', and 7', and combinations thereof.

The present invention provides a composition of the Formula 16:

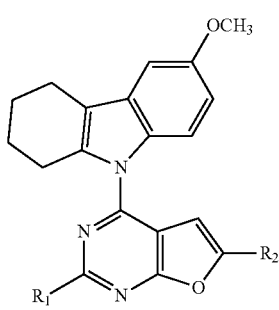

16 comprising wherein R$_1$ is selected from the group consisting of H, NH$_2$, and a straight chain or branched chain alkyl group having from 1 to 10 carbon atoms; and wherein R$_2$ is selected from the group consisting of H and a straight chain or branched chain alkyl group having from 1 to 10 carbon atoms; and optionally comprising stereochemical conformations thereof; and optionally comprising a pharmaceutically acceptable salt thereof. A preferred embodiment of the compositions embodied by Formula 16 is set forth in Series XXIII(c), FIG. 12, identified by Composition 145.

Water soluble salts, such as for example HCL salts (or other acids), of the compositions of Formulae 1-5, 7-21, 24, 32, 33 and 35 of the present invention (as set forth in FIGS. 1-13) are also provided herein.

A method of treating a patient having cancer is provided herein comprising administering to a patient an effective amount of a composition of the present invention as identified by any one or more of the compositions of the present invention, for example, the compositions of Formulae 1-5, 7-21, 24, 32, 33, and 35, and salts thereof, for treating the patient. In another embodiment of this invention, a method of treating a patient with macular degeneration or arthritis is disclosed herein comprising administering to a patient an effective amount of a composition of the present invention as identified by any one or more of Formulae 1-5, 7-21, 24, 32, and 35, and salts thereof, for treating the patient having macular degeneration or arthritis. Another embodiment of the present invention provides a method of treating a patient having cancer comprising inhibiting VEGFR2 receptors and tubulin assembly by administering a therapeutically effective amount of at least one composition of Formulae 1-5, 7-21, 24, 32, 33, and 35, to the patient for effecting treatment of the patient.

Synthesis of Compositions

Compound E (FIG. 18) was synthesized from benzaldehyde using a reported procedure known by those persons skilled in the art. Compound E (FIG. 18), when treated with acetonitrile, afforded the bicyclic Compound F which was chlorinated with POCl$_3$ to yield Compound G. Nucleophilic displacement of the 4-Cl group with commercially available compound H and formation of the HCl salt afforded the HCl salt formulation of Composition 104 (RP249).

All intermediates and final compounds were analyzed by melting point, TLC, NMR, HRMS and/or elemental analysis and chromatography for purity and characterization. The intermediate and final compounds may be used to synthesize the analog compositions.

Highly water soluble salts of the compositions of the present invention are easily obtained by those persons skilled in the art. Compositions of the present invention in all Series (except Series XI), all contain basic nitrogens and can easily form acids salts as shown in Schemes A-C (FIG. 18) for the compositions of the present invention.

The synthesis of the compositions in Series I, II, III, IV, VIII, X through XVIII, XX, and XXII through XXIV (structures presented in FIGS. 1-13) as their HCl salts may be conducted using modified methods outlined in Scheme A for the present compositions of Series I, II, III, IV, VIII, and X, Scheme B for the present compositions of Series XII through XVII, and Scheme C for the present compositions of Series XVIII, XX, and XXII through XXIV. Generally the synthetic methods involve the synthesis of the parent scaffold with a 4-oxo functionality that is easily converted to the 4-chloro with POCl$_3$. The parent scaffolds for all the Series compositions set forth in FIGS. 1-13 are either in Schemes A-C or commercially available or available directly from literature methods. Suitable method modifications of Schemes A, B, and C as are known by those persons skilled in the art and obtainable from available literature references provide for the structures of the compositions of FIGS. 1-13. Displacement of the 4-chloro derivative with appropriate anilines as in Schemes A-C should afford most of the 4-substituted compounds. In addition, alternate Pd or Cu catalyzed cross coupling reactions of the Buchwald type with the aniline and the 4-halo derivative can also be employed for this reaction. Water soluble HCl or other acid salts made by methods outlined in Schemes A-C for the HCl salt are also simple and easily obtained. These synthesis methods are routine as well as well documented in the literature. Bulk synthesis of the compositions of the present invention as set forth in FIGS. 1-13 selected for animal studies will follow routine synthetic methods.

Synthesis of Composition 106 (C Ring Aromatic) as the HCl Salt

Referring to FIG. 24, Scheme A:

2-methyl-3H-pyrimido[5,4-b]indol-4(5H)-one (E)

is shown in FIG. 24, Scheme A. HCl gas was bubbled through a stirred solution of A (1 g, 4.9 mmol) in acetonitrile (20 mL) for 3 h. Most of the solvent was removed in vaccuo. The residue was dissolved in 10 mL distilled water and the pH was adjusted to 8 with aq. ammonia solution to generate a yellow suspension which was filtered. The collected solid was dried in vacuum using $P_2O_5$ to afford 730 mg (75%) of E as a light yellow powder. $^1$H NMR (DMSO-$d_6$): δ 2.43 (s, 3H), 7.19 (t, 1H), 7.43 (t, 1H), 7.50 (d, 1H), 7.959 (d, 1H), 11.90 (s, 1H), 12.268 (s, 1H)

4-chloro-2-methyl-5H-pyrimido[5,4-b]indole (F)

To a 50 mL flask was added E (600 mg, 3.01 mmol) and 15 mL $POCl_3$. The resulting mixture was heated to reflux for 4 h, and the solvent was removed under reduced pressure, pH adjusted to 8 using aq. ammonia solution to afford a light brown suspension. The precipitate was collected by filtration to afford 480 mg (73%) of F as a yellow solid. $^1$H NMR (DMSO-$d_6$): δ 2.75 (s, 3H), 7.34 (t, 1H), 7.67 (m, 2H), 8.22 (d, 1H), 12.201 (s, 1H)

4-(6-methoxy-3,4-dihydroquinolin-1(2H)-yl)-2-methyl-5H-pyrimido[5,4-b]indole hydrochloride (Composition No. 106. HCl)

To a 50 mL flask was added F (100 mg, 459.44 μmol), H (90 mg, 551.33 μmol) and 10 mL isopropanol. The mixture was heated to reflux for 24 h and the solvent was removed under reduced pressure. To the residue obtained was added silica gel and MeOH and the solvent removed. The resulting plug was loaded on to a silica gel column with 1% MeOH in $CHCl_3$ as the eluent. Fractions that showed the desired spot (TLC $R_f$=0.5 in 1:10 MeOH:$CHCl_3$) were pooled, and the solvent evaporated to dryness to afford a residue. To this residue was added ethylacetate (1 mL) and diethylether (10 mL), and HCl gas was bubbled at room temperature for 5 mins to afford 134 mg (76.6%) of Composition No. 106. HCl. $^1$H NMR (DMSO-$d_6$): δ 2.075 (m, 2H), 2.80 (s, 3H), 2.87 (t, 2H), 3.82 (t, 2H) 4.2 (s, 3H), 6.78 (d, 1H), 7.0 (d, 1H), 7.11 (s, 1H), 7.35 (t, 1H), 7.63 (m, 2H), 8.46 (d, 1H), 10.85 (s, 1H), 15.96 (s, 1H) Anal. Calcd. for $C_2H_{21}ClN_4O$. 0.3; $H_2O$:C, 65.30; H, 5.64; N, 14.50; Cl, 19.18. Found C, 65.37; H, 5.50; N, 14.48; Cl, 9.06.

Synthesis of Composition No. 125

Referring to FIG. 24, Scheme C:

2-Methyl-5-prop-2-yn-1-ylpyrimidine-4,6-diol (K)

50 mL anhydrous MeOH was added to a 250 mL flask, I (3.96 g, 2 mmol) and J (1.85 g, 2 mmol) were dissolved in this solution. After 800 mg (2 mmol) Na was added to the solution, yellow precipitate was observed. The resulting mixture was refluxed overnight. The yellow precipitate was collected by filtration and then dissolved in 10 mL $H_2O$. The pH of the resulting solution was adjusted to 6.5 by adding 2 N HCl to afford a yellow precipitate, which was collected by filtration and dried over $P_2O_5$ to afford 1.21 g (37%) K; mp>300° C.; $R_f$ 0.11 ($CHCl_3$/MeOH 6:1); $^1$H NMR (DMSO-$d_6$) δ 2.23 (s, 3H), 3.05 (s, 2H), 3.32 (s, 1H), 11.92 (s, 2H).

2,6-Dimethylfuro[2,3-d]pyrimidin-4(3H)-one (L)

1.64 g (1 mmol) K was added to 15 mL $H_2SO_4$ (conc.) The solution was stirred overnight and poured in to 100 mL distilled water and extracted by 3×30 mL $CHCl_3$. The organic layer was pooled and concentrated to afford 1.36 (83%) L as a yellow powder; mp>300° C.; $R_f$ 0.35 ($CHCl_3$/MeOH 6:1); $^1$H NMR (DMSO-$d_6$) δ 2.42 (s, 3H), 2.44 (s, 3H), 6.63 (s, 1H), 12.50 (s, 1H).

4-Chloro-2,6-dimethylfuro[2,3-d]pyrimidine (M)

To a 50 mL flask was added 1.64 g (1 mmol) L and 10 mL $POCl_3$. The resulting mixture was refluxed for 2 h, and the solvent was removed under reduced pressure to afford a dark residue. To this was added 30 mL of $CHCl_3$ and 3 g of silica gel. The solvent was evaporated to afford a plug. Column chromatography of the plug with hexane:acetyl acetate=20:1 as eluent afford 1.55 g (85%) M as a yellow solid; $R_f$ 0.26 (Hexane/EtOAC 15:1); $^1$H NMR (DMSO-$d_6$) δ 2.48 (s, 3H), 2.63 (s, 3H), 6.77 (s, 1H).

2,6-Dimethyl-N-[4-(methylsulfanyl)phenyl]furo[2,3-d]pyrimidin-4-amine (N)

To a 50 mL flask was added M (91 mg, 0.5 mmol), 4-(methylsulfanyl)aniline (76 mg, 0.55 mmol) and i-PrOH (5 mL). To this solution was added 2 drops of concentrated HCl solution and the mixture was refluxed. TLC indicated the disappearance of starting material 5, the solvent was removed under reduced pressure. To the residue obtained was added silica gel and MeOH and the solvent removed to make a plug. This plug was separated by column chromatography to give 97 mg (68%) of 7 as a yellow powder; $R_f$ 0.4 (Hexane/EtOAC 3:1); $^1$H NMR (DMSO-$d_6$) δ 2.43 (s, 3H), 2.48 (s, 3H), 2.49 (sq, 3H), 6.70 (s, 1H), 7.28-7.30 (d, 2H), 7.78-7.80 (d, 2H), 9.51 (s, 1H); Anal. Calcd. for $C_{15}H_{15}N_3OS$:C, 63.13; H, 5.30; N, 14.73; S, 11.24. Found C, 62.99; H, 5.27; N, 14.56; S, 11.10.

N,2,6-Trimethyl-N-[4-(methylsulfanyl)phenyl]furo[2,3-d]pyrimidin-4-amine (Composition No. 125)

To a 25 mL round bottom flask was weighed N (143 mg, 0.5 mmol) and was added DMF (2 mL) to afford a solution. The flask was purged with argon for five min followed by cooling down to 0° C. using ice bath. Sodium hydride (36 mg, 1.5 mmol) was added to the solution at 0° C. The solution was stirred for 30 min at 0° C. under argon atmosphere. Dimethyl sulfate (150 mg, 1.2 mmol) was introduced to the reaction mixture with the help of a syringe and the flask was warmed to room temperature. The mixture was stirred at room temperature for another 3 h at the end of which 1 N hydrochloric acid (5 mL) was added carefully to quench the reaction. The reaction solvent was removed under reduced pressure and the residue was suspended in water (20 mL). The suspension was extracted using ethyl acetate (10 mL×2). Combined organic extracts were washed with brine (10 mL) dried (anhydrous sodium sulfate) and concentrated under reduced pressure. Silica gel (200 mg) was added and solvent evaporated to afford a plug. Column chromatography by elution with hexane:ethyl acetate (5:1) afforded 78 mg (52%) of Composition No. 125 as a light yellow solid: $R_f$ 0.5 (AcOEt/Hexane, 1:3); $^1$H NMR (DMSO-d6) δ 2.18 (s, 3H), 2.49 (s, 3H), 2.54 (s, 3H), 3.47 (s, 3H), 4.73 (s, 1H), 7.30-7.32 (d, 2H), 7.38-7.39 (d, 2H); Anal. Calcd. for $C_{16}H_{17}N_3OS$:C, 64.19; H, 5.72; N, 14.04; S, 10.71. Found C, 64.26; H, 5.68; N,13.90; S, 10.80.

Prophetic Synthesis of Compositions of the Present Invention

Referring to FIG. 25, Scheme 1:

4-Chloro group on the pyrimidine heterocycles can be displaced by appropriate nucleophiles under various conditions. The typical reaction procedure for the displacement of 4-Cl by substituted anilines is to dissolve the two reaction partners in iPrOH, add 1-2 drops of HCl (conc.) and then heat the reaction solution to reflux for 24 h. For certain reactions, the conditions can further be optimized. Such variations include the changes from iPrOH to BuOH, from HCl (conc.) to $H_2SO_4$ (conc.) or the changes from bench-top reactions to microwave assisted conditions. For the displacement of 4-Cl by heterocyclic nucleophiles, similar displacement reactions as well as some Pd- or Cu-catalyzed coupling reactions can be adopted. See, for example, Xi, Z.; Liu, F.; Zhou, Y.; Chen, W. CuI/L (L=Pyridine-functionalized 1,3-Diketones) Catalyzed C—N Coupling Reactions of Aryl Halides with NH-containing Heterocycles. *Tetrahedron* 2008, 64, 4254-4259; and Lagisetty, P.; Russon, L. M.; Lakshman, M. K. A General Synthesis of C6-azolyl Purine Nucleosides. *Angew. Chem. Int. Ed.* 2006, 45, 3660-3663.

Referring to FIG. 25, Scheme 2:

Commercially available 158 (Scheme 2, FIG. 25) can be converted to 159 by reductive amination which on treatment with C (Scheme A) should afford 4. See, for example, Baxter, E. W.; Reitz, A. B. Reductive Aminations of Carbonyl Compounds with Borohydride and Borane Reducing Agents. In *Organic Reactions*; Overman, L. E., Eds., Wiley & Sons: New York, 2002; Vol. 59, pp 1-170; and Gangjee, A.; Zhao, Y.; Lin, L.; Raghavan, S.; Roberts, E. G.; Risinger, A. L.; Hamel, E.; Mooberry, S. L. Synthesis and Discovery of Water-soluble Microtubule Targeting Agents that Bind to the Colchicine Site on Tubulin and Circumvent Pgp Mediated Resistance. *J. Med. Chem.* 2010, 53, 8116-8128.

Referring to FIG. 25, Scheme 3:

Methylation of commercially available 160 (Scheme 3, FIG. 25) with methyl iodide will afford 161. Compounds 160 and 161 on catalytic hydrogenation will afford 162 and 163 respectively. Compounds 162, 163 and commercially available 164 can be converted to 165-167 respectively which on treatment with C (Scheme A, FIG. 24) should afford Composition Nos. 5-7 respectively. Treatment of C with ammonia should afford 168 which on Pd-catalyzed coupling with 169 will afford Composition No. 8. See for example, Johansen, M. B.; Kerr, M. A. Direct Functionalization of Indoles: Copper-catalyzed Malonyl Carbenoid Insertions. *Org. Lett.* 2010, 12, 4956-4959; Makuc, D.; Triyanti; Albrecht, M.; Plavec, J.; Rissanen, K.; Valkonen, A.; Schalley, C. A. The Halide Binding Behavior of 2-Carbamoyl-7-ureido-1H-indoles: Conformational Aspects. *Eur. J. Org. Chem.* 2009, 28, 4854-4866; Gangjee, A.; Zaware, N.; Raghavan, S.; Ihnat, M.; Shenoy, S.; Kisluik, R. L. Single Agents with Designed Combination Chemotherapy Potential: Synthesis and Evaluation of Substituted Pyrimido [4,5-b]indoles as Receptor Tyrosine Kinase and Thymidylate Synthase Inhibitors and as Antitumor Agents. *J. Med. Chem.* 2010, 53, 1563-1578; and Ngassa, F. N.; DeKorver, K. A.; Melistas, T. S.; Yeh, E. A.-H.; Lakshman, M. K. Pd-xantphos-catalyzed Direct Arylation of Nucleosides. *Org. Lett.* 2006, 8, 4613-4616.

Referring to FIG. 26, Scheme 5:

Commercially available indoles 183 and 184 (Scheme 5, FIG. 26) can be treated with NaH and C (Scheme A) to afford Composition Nos. 15 and 16 respectively. See for example, Dunn, J. P.; Goldstein, D. M.; Gong, L.; Hogg, J. H.; Michoud, C.; Palmer, W. S.; Sidduri, A.; Silva, T.; Tivitmahaisoon, P.; Trejo-Martin, T. A. Preparation of Pyrimidines as c-Jun N-Terminal Kinase (JNK) Modulators. PCT Int. Appl. 068171, 2008.

Compound C (Scheme A, FIG. 24) can be treated with commercially available 185-(±)186 to afford Composition Nos. 17-(±)18 respectively.

Referring to FIG. 26, Scheme 26:

Stille coupling of C (Scheme A, FIG. 24) with 190 (Scheme 6, FIG. 26) and commercially available 192 should afford 191 and 193 respectively. Reductive amination of 191 and 193 with D (Scheme A, Preliminary Studies) should afford 22 and (±)23 respectively. Reductive amination of 191 with p-anisidine should afford (±)24. See for example, Bender, J. A.; Yang, Z.; Kadow, J. F.; Meanwell, N. A. Diazaindole-dicarbonyl-piperazinyl Antiviral Agents. U.S. Pat. Appl. 0124623, 2005; and Baker, S. J.; Goldsmith, P. J.; Hancox, T. C.; Pegg, N. A.; Shuttleworth, S. J.; Dechaux, E. A.; Krintel, S. L.; Price, S.; Large, J. M.; McDonald, E. 2-(Morpholin-4-yl)pyrimidine Derivatives as PI3K Inhibitors and their Preparation, Pharmaceutical Compositions and use in the Treatment of Diseases. PCT Int. Appl. 125833, 2008.

Referring to FIG. 26, Scheme 7:

Analogous to A (Scheme A, FIG. 24), compounds 195 (Scheme 7, FIG. 26) can be converted to 27. See for example, Morris Jr., P. E.; Elliott, A. J.; Montgomery, J. A. New Syntheses of 7-Substituted-2-aminothieno- and Furo [3,2-d]pyrimidines. *J. Heterocycl. Chem.* 1999, 36, 423-427.

Referring to FIG. 27, Scheme 12:

Compound 213 (Scheme 12, FIG. 27) can be reacted with commercially available 215-222 (Scheme 13, FIG. 27) to afford compositions with general structure of Composition No. 223 analogous to E (Scheme A, FIG. 24) which can be converted to Composition Nos. 50-57. Composition Nos. 50-57 can be methylated to afford Composition Nos. 58-65.

Referring to FIG. 28, Scheme 15:

Using a reported methodology of Elliott, A. J.; Morris Jr., P. E.; Petty, S. L.; Williams, C. H. An Improved Synthesis of 7-Substituted Pyrrolo[3,2-d]pyrimidines. *J. Org. Chem.* 1997, 62, 8071-8075, commercially available compositions 231, 234-239 (Scheme 15, FIG. 28) can be converted to compounds with general structure of composition 240 analogous to A (Scheme A, FIG. 24) which can be treated with acetonitrile and HCl to afford the corresponding bicyclics which on chlorination and subsequent displacement with D (Scheme A, FIG. 24) will afford Composition Nos. 74, 77-82. Composition Nos. 74, 77-82 can be methylated to afford Composition Nos. 83, 86-91.

Referring to FIG. 28, Scheme 16:

Compounds 244 and 245 (Scheme 16, FIG. 28) can be prepared from commercially available compositions 241 and 242 by palladium-catalyzed benzylic C—H borylation. See for example, Giroux, A. Synthesis of Benzylic Boronates via Palladium-Catalyzed Cross-Coupling Reaction of Bis(pinacolato)diboron with Benzylic Halides. *Tetrahedron Lett.* 2002, 44, 233-235. Compounds 244 and 245 on Suzuki coupling (see Havelková, M.; Dvořák, D.; Hocek, M. The Suzuki-Miyaura Cross-coupling Reactions of 2-, 6- or 8-Halopurines with Boronic Acids Leading to 2-, 6- or 8-Aryl- and -Alkenylpurine Derivatives. *Synthesis* 2001, 1704-1710) with G (Scheme A, FIG. 24) affords Composition Nos. (±)92 and (±)93 respectively. Commercially available 246 and 247 (Scheme 17, FIG. 28) can be deprotonated using sodium hydride and treated with G (Scheme A, FIG. 24) to afford Composition Nos. 94-95 which on methylation affords Composition Nos. 96-97. Composition 104 (RP 249) can be methylated using sodium hydride and methyl iodide to afford Composition 98.

Referring to FIG. 29, Scheme 18:

Analogous to A (Scheme A, FIG. 24) commercially available 248 (Scheme 18, FIG. 29) can be treated with acetonitrile and HCl to afford the corresponding bicyclic which on chlorination and subsequent displacement with H will afford Composition 99. Analogous to E (Scheme A, FIG. 24), compound 249 (see for example, Ren, W.-Y.; Rao, K. V. B.; Klein, R. S. Convenient Synthesis of Substituted 3-Aminothiophene-2-carbonitriles from α-Acetylenic Nitriles and their conversion to thieno[3,2-d]pyrimidines. *J. Heterocycl. Chem.* 1986, 23, 1757-1763) on chlorination and subsequent displacement with H (Scheme A, FIG. 24) will afford Composition No. 100.

Compounds 253-255 (Scheme 18, FIG. 29) can be prepared from 250-252 by a known methodology (see, Gangjee, A.; Li, W.; Yang, J.; Kisliuk, R. L. Design, Synthesis, and Biological Evaluation of Classical and Nonclassical 2-Amino-4-oxo-5-substituted-6-methylpyrrolo[3,2-d]pyrimidines as Dual Thymidylate Synthase and Dihydrofolate Reductase Inhibitors. *J. Med. Chem.* 2008, 51, 68-76). Analogous to A (Scheme A, FIG. 24), compounds 253-255 can be converted to Composition Nos. 101-103.

Referring to FIG. 29, Schemes 19, 20, and 21:

Compounds 213 and 214 (Scheme 12, FIG. 27) can be reacted with Al(CH$_3$)$_3$ to afford 256 and 257 (Scheme 19, FIG. 29) which on chlorination and subsequent displacement with H will afford Composition Nos. 104-105. See for example, Hocek, M.; Pohl, R.; Cisarová, I. Highly Methylated Purines and Purinium Salts as Analogs of Heteromines. *Eur. J. Org. Chem.* 2005, 3026-3030.

Commercially available 258 (Scheme 20, FIG. 29) on chlorination with phosphorous oxychloride will afford 259 which on treatment with the carbanion of cyclohexanone will afford 260. See for example, Thurkauf, A.; Hutchison, A. Certain Aryl Fused Pyrrolopyrimidines; a new Class of GABA Brain Receptor Ligands, U.S. Pat. No. 5,326,868, 1994. Compound 260 on cyclization affords 261. See for example, U.S. Pat. No. 5,326,868. On treatment with H (Scheme A, FIG. 24), 261 affords Composition No. 106.

Treatment of G (Scheme A, FIG. 24) with commercially available (±)186 (Scheme 5, FIG. 26), 263-264, 185 (Scheme 5, FIG. 26), 265-268, easily accessible 269, 270 (see Yamada, K.; Somei, M. Photo-induced Rearrangement of 1-Ethoxy-2-phenylindole. *Heterocycles* 1998, 48, 2481-2484) affords Composition Nos. (±)107, 108-109, 110, 112-115, 116 (after silyl deprotection) and 118 respectively. Composition No. 110 on methylation will afford Composition No. 111. The O-demethylation of Composition No. (±)114 using BBr$_3$ yields Composition No. (±)117. See for example, McOmie, J. F. W.; Watts, M. L.; West, D. E. Demethylation of Aryl Methyl Ethers by Boron Tribromide. *Tetrahedron* 1968, 24, 2289-2292.

Analogous to A (Scheme A, FIG. 24), compound 272 can be treated with acetonitrile and HCl to afford the corresponding bicyclic which on chlorination and subsequent displacement with D (Scheme A, FIG. 24) will afford Composition Nos. 119 and 121 respectively. Composition No. 119 on methylation affords Composition No. 120.

Referring to FIG. 30, Scheme 22:

Treatment of 303 (Scheme 22, FIG. 30) with malononitrile will afford 276, which can be treated with acetonitrile and HCl to yield 279. See for example, Matsuda, T.; Yamagata, K.; Yukihiko, T.; Yamazaki, M. Studies on Heterocyclic Enaminonitriles. VI. Synthesis of 2-Amino-3-cyano-4,5-dihydrofurans. *Chem. Pharm. Bull.* 1985, 33, 937-943. Coupling between 279 and 4-methoxy iodobenzene using copper (I) iodide and L-proline as a chelating ligand in the presence of potassium carbonate affords 282. See for example Guo, X.; Rao, H.; Fu, H.; Jiang, Y.; Zhoa, Y. An Inexpensive and Efficient Copper Catalyst for N-Arylation of Amines, Amides and Nitrogen-containing Heterocycles. *Adv. Synth. Catal.* 2006, 348, 2197-2202. Reductive amination of 282 will afford Composition No. 138 (C ring saturated). Composition No. 138 (C ring saturated) can be treated with 10% Palladium on carbon or manganese dioxide to provide Composition No. 138 (C ring aromatic). See for example, Nakamichi, N.; Kawashita, Y.; Hayashi, M. Oxidative Aromatization of 1,3,5-Trisubstituted Pyrazolines and Hantzsch 1,4-Dihydropyridines by Pd/C in Acetic Acid. *Org. Lett.* 2002, 4, 3955-3957.

Treatment of M (Scheme C, FIG. 24) with commercially available (±)186 (Scheme 5, FIG. 26), 263-264 (Scheme 21, FIG. 30), 246-247 (Scheme 17, FIG. 28), 265-268 easily accessible 269, 270 (see for example, Yamada, K.; Somei, M. Photo-induced Rearrangement of 1-Ethoxy-2-phenylindole. *Heterocycles* 1998, 48, 2481-2484) (Scheme 21, FIG. 30) affords Composition Nos. (±)139, 140-141, 142-143, 144-147, 148 (after silyl deprotection) and 150 respectively. The O-demethylation of Composition No. (±)148 using BBr$_3$ yields Composition No. (±)150. See for example, McOmie, J. F. W.; Watts, M. L.; West, D. E. Demethylation of Aryl Methyl Ethers by Boron Tribromide. *Tetrahedron* 1968, 24, 2289-2292.

Biological Evaluation

TABLE 1

Tumor cell inhibitory activity (NCI) GI$_{50}$ (nM) of Composition No. 104.

| Panel/Cell line | GI$_{50}$ (nM) Composition |
|---|---|
| Leukemia | 104 |
| CCRF-CEM | 35.1 |
| HL-60(TB) | 26.2 |
| K-562 | 41.5 |
| MOLT-4 | 98.3 |
| RPMI-8226 | 42.9 |
| SR | 30.9 |
| NSCLC | |
| A549/ATCC | 40.1 |
| EKVX | 99.6 |
| HOP-62 | 45.3 |
| HOP-92 | 59.5 |
| NCI-H226 | 82.3 |
| NCI-H23 | 71.0 |
| NCI-H322M | 44.2 |
| NCI-H460 | 36.9 |
| NCI-H522 | |
| Colon Cancer | 104 |
| COLO 205 | 27.4 |
| HCC-2998 | 86.0 |
| HCT-116 | 39.2 |
| HCT-15 | 42.1 |
| HT29 | 37.7 |
| KM12 | 35.6 |
| SW-620 | 39.8 |
| CNS Cancer | |
| SF-268 | 62.6 |
| SF-295 | 16.6 |
| SF-539 | 25.4 |
| SNB-19 | 50.3 |
| SNB-75 | 38.0 |
| U251 | 39.9 |
| Melanoma | 104 |

TABLE 1-continued

Tumor cell inhibitory activity (NCI) GI$_{50}$ (nM) of Composition No. 104.

| Panel/Cell line | GI$_{50}$ (nM) Composition |
|---|---|
| LOX IMVI | 72.5 |
| M14 | 29.4 |
| MDA-MB-435 | 17.0 |
| SK-MEL-2 | 56.5 |
| SK-MEL-28 | 74.9 |
| SK-MEL-5 | 48.6 |
| UACC-62 | 48.4 |
| Ovarian cancer | |
| IGROVI | 47.0 |
| OVCAR-3 | 22.7 |
| OVCAR-4 | 96.6 |
| OVCAR-5 | 60.7 |
| OVCAR-8 | 43.9 |
| NCI/ADR-RES | 29.4 |
| SK-OV-3 | 33.9 |
| Renal Cancer | |
| 786-0 | 63.1 |
| A498 | 24.3 |
| ACHN | 70.1 |
| CAKI-1 | 42.3 |
| RXF 393 | 28.9 |
| SN12C | 84.9 |
| TK10 | |
| UO-31 | 54.3 |
| Prostate Cancer | |
| PC-3 | 50.4 |
| DU-145 | 34.9 |
| Breast Cancer | |
| MCF7 | 38.0 |
| MDA-MB-231/ATCC | 101 |
| HS 578T | 30.2 |
| BT-549 | 218 |
| MDA-MB-468 | 23.4 |

NCI (National Cancer Institute) 60 Tumor Panel (Table 1).

Composition 104 of the present invention shows a remarkable 2-digit nanomolar GI$_{50}$ in all the NCI 60 tumor cell lines.

Compositions of the present invention are effective and potent inhibitors of bovine tubulin assembly (Composition 104, Table 2). This provides direct evidence of interaction of Composition 104 with tubulin. Composition 104 of the present invention is comparable to combretastatin (CA). In addition, Composition 104 is also a potent inhibitors of [$^3$H]colchicine binding (Table 2), thus, indicating that the compositions of the present invention bind at the colchicine binding site on tubulin similar to CA. Composition 104 was also evaluated against epidermal growth factor receptor (EGFR), vascular endothelial growth factor receptor (VEGFR2) and platelet derived growth factor receptor-β (PDGFR-β) (Table 2). The tyrosine kinase inhibitory values (Table 2) are compared with standards sunitinib and semaxinib (VEGFR2), erlotinib (PDGFR-13 and EGFR), DMBI (PDGFR-β) and PD153035 (EGFR). DMBI is a potent inhibitor of tyrosine kinase activities of the PDGFβ-receptor. DMBI (commercially available from EMD Chemicals, Inc., Gibbstown 08027, USA) does not inhibit EGFR even at concentrations greater than 100 μM. Composition 104 of the present invention has comparable potency as sunitinib and semaxinib against VEGFR2 (Table 2). However, Composition 104 is a relatively poor inhibitor of EGFR and PDGFR-β, compared to standards. In order to rule out off target toxicity, Composition 104 was evaluated in a kinase profiling service (Luceome Biotechnologies) against 50 other kinases and found no activity at 10 μM. Composition 104 is unlikely to be Pgp or MRP substrates, and it possesses relative selectivity of kill on tumor versus normal cell types.

FIG. 16 shows that Compositions No. 104 and 106 of the present invention are potent inhibitors of EGFR kinase, Flk-1 (VEGR2) kinase, and PDGFR kinase, and that each are comparable to sunitinib.

Molecular Modeling and Computational Studies.

The structural basis of the inhibition of tubulin at the colchicine binding site of Composition 104 was determined. The X-ray crystal structure of αβ-tubulin at 3.58Å resolution (PDB ID 1SAO) complexed with DAMA colchicine, was used. Pharmacophores of the various small molecule colchicine-site binders have been determined. Docking of Composition 104 and its respective analog compositions having the structural formulae set forth in FIGS. 1-13 for scaffold analogs Series I, II, III, IV, VIII, X-XVIII, XX, and XXII-XXIV into the colchicine binding site have been accom-

TABLE 2

Inhibition of tubulin assembly, $^3$H-colchicine binding and kinase inhibition IC$_{50}$ (μM) for Composition No. 104

| COMPOSITION | Inhibition of tubulin assembly IC$_{50}$ (μM) | colchicine binding (1 μM) | (5 μM) | kinase inhibition IC$_{50}$(μM) | | |
|---|---|---|---|---|---|---|
| | | | | EGFR | VEGFR2 | PDGFRβ |
| | 5 | | | | | |
| 104 | 1.2 ± 0.007 | 76 ± 0.5 | | 20.2 ± 3.8 | 30.6 ± 4.5 | 82.3 ± 10.3 |
| CA$^a$ | 1.2 ± 0.01 | 98 ± 0.3 | | | | |
| PD153035 | | | | 0.21 ± 0.002 | | |
| Semaxinib | | | | | 12.9 | |
| DOX | | | | | | |
| cisplatin | | | | | | |
| sunitinib | | | | 172.1 ± 19.4 μM | 18.9 ± 2.7 | 83.1 ± 10.1 |
| erlotinib | | | | 1.2 ± 0.2 μM | 124.7 ± 18.2 | 12.2 ± 1.9 |
| DMBI | | | | | | 3.75 |

$^a$CA = combretastatin; DOX = doxirubicin; DMBI = inhibitor of PDGRβ plished. In addition, using the VEGFR2 X-ray crystal structure, we have docked Composition 104 and analogs thereof in VEGFR2. In addition, pharmacophore models using SYBYL have been determined from IC$_{50}$ values for antitubulin and for other antitumor agents. We employ programs implemented in MOE and SYBYL 8.2 along with docking programs from MOE, SYBYL Glide, Gold among others. These programs allow the generation of pharmacophores and COMFA and COMISA. The relation of tumor cell inhibition data and the pharmacophore generation employs literature methods that have been successfully used for antitubulins as well as other antitumor agents using SYBYL.

It will be appreciated by those persons skilled in the art that changes could be made to embodiments of the present invention described above without departing from the broad inventive concept thereof. It is understood, therefore, that this invention is not limited by any particular embodiments disclosed, but is intended to cover the modifications that are within the spirit and scope of the invention, as defined by the appended claims.

What is claimed is:

1. A compound of Formula 5:

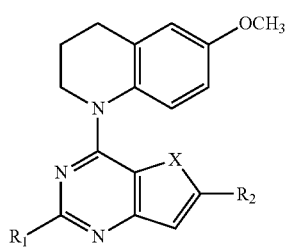

wherein $R_1$ is selected from the group consisting of H, $NH_2$, and a straight chain or branched chain alkyl group having from 1 to 10 carbon atoms; and
wherein $R_2$ is selected from the group consisting of H and a straight chain or branched chain alkyl group having from 1 to 10 carbon atoms; and
wherein X is O; and
stereochemical conformations thereof; and
a pharmaceutically acceptable salt thereof.

2. A pharmaceutical composition comprising a therapeutically effective amount of a compound of Formula 5:

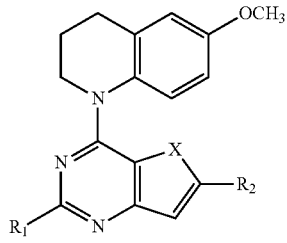

wherein $R_1$ is selected from the group consisting of H, $NH_2$, and a straight chain or branched chain alkyl group having from 1 to 10 carbon atoms; and
wherein $R_2$ is selected from the group consisting of H and a straight chain or branched chain alkyl group having from 1 to 10 carbon atoms; and
wherein X is O; and
stereochemical conformations thereof; and
a pharmaceutically acceptable salt thereof.

3. The pharmaceutical composition according to claim 2 comprising at least one pharmaceutically acceptable carrier.

4. A method of treating a patient having a disease by administering a therapeutically effective amount of at least one compound of Formula 5:

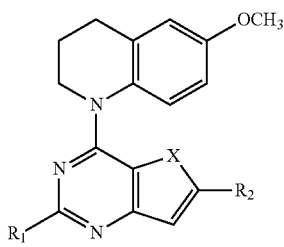

wherein $R_1$ is selected from the group consisting of H, $NH_2$, and a straight chain or branched chain alkyl group having from 1 to 10 carbon atoms; and
wherein $R_2$ is selected from the group consisting of H and a straight chain or branched chain alkyl group having from 1 to 10 carbon atoms; and
wherein X is O; and
stereochemical conformations thereof; and
a pharmaceutically acceptable salt thereof, wherein said disease is cancer.

5. A compound of Formula 35:

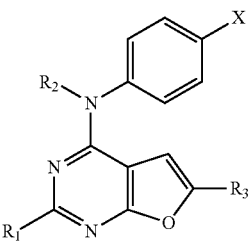

wherein $R_1$ is selected from the group consisting of H, $NH_2$, and a straight chain or branched chain alkyl group having from 1 to 10 carbon atoms; and
wherein $R_2$ is selected from the group consisting of H and a straight chain or branched chain alkyl group having from 1 to 10 carbon atoms; and
wherein $R_3$ is selected from the group consisting of H and a straight chain or branched chain alkyl group having from 1 to 10 carbon atoms; and
wherein X is $SCH_3$, and
stereochemical conformations thereof; and
a pharmaceutically acceptable salt thereof.

6. A pharmaceutical composition comprising a therapeutically effective amount of a compound of Formula 35:

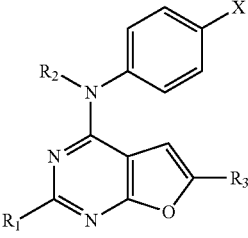

wherein $R_1$ is selected from the group consisting of H, $NH_2$, and a straight chain or branched chain alkyl group having from 1 to 10 carbon atoms; and wherein $R_2$ is selected from the group consisting of H and a straight chain or branched chain alkyl group having from 1 to 10 carbon atoms; and wherein $R_3$ is selected from the group consisting of H and a straight chain or branched chain alkyl group having from 1 to 10 carbon atoms; and wherein X is $SCH_3$, and stereochemical conformations thereof; and a pharmaceutically acceptable salt thereof.

7. A pharmaceutical composition according to claim 6 comprising at least one pharmaceutically acceptable carrier.

* * * * *